(12) United States Patent
Broka et al.

(10) Patent No.: US 8,895,589 B2
(45) Date of Patent: Nov. 25, 2014

(54) PYRIDINYL AMIDES AS P2X3 AND P2X2/3 INHIBITORS

(75) Inventors: Chris Allen Broka, Las Vegas, NV (US); Ronald Charles Hawley, Glen Ridge, NJ (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 13/592,625

(22) Filed: Aug. 23, 2012

(65) Prior Publication Data
US 2013/0165443 A1 Jun. 27, 2013

Related U.S. Application Data

(62) Division of application No. 12/820,577, filed on Jun. 22, 2010, now Pat. No. 8,283,383.

(60) Provisional application No. 61/219,016, filed on Jun. 22, 2009.

(51) Int. Cl.

| | | |
|---|---|---|
| *A61K 31/4418* | (2006.01) | |
| *C07D 213/24* | (2006.01) | |
| *C07D 405/14* | (2006.01) | |
| *C07D 417/12* | (2006.01) | |
| *C07D 307/68* | (2006.01) | |
| *C07D 265/30* | (2006.01) | |
| *C07D 403/12* | (2006.01) | |
| *C07D 261/18* | (2006.01) | |
| *C07D 213/56* | (2006.01) | |
| *C07D 263/34* | (2006.01) | |
| *C07D 213/61* | (2006.01) | |
| *C07D 277/56* | (2006.01) | |
| *C07C 237/42* | (2006.01) | |
| *C07D 333/38* | (2006.01) | |
| *C07D 213/81* | (2006.01) | |
| *C07D 241/24* | (2006.01) | |
| *C07C 237/32* | (2006.01) | |
| *C07D 241/12* | (2006.01) | |
| *C07D 309/08* | (2006.01) | |
| *C07D 231/14* | (2006.01) | |
| *C07D 285/06* | (2006.01) | |
| *C07D 295/125* | (2006.01) | |
| *C07D 401/12* | (2006.01) | |

(52) U.S. Cl.
CPC ............ *C07C 237/42* (2013.01); *C07D 405/14* (2013.01); *C07D 417/12* (2013.01); *C07C 2101/02* (2013.01); *C07D 307/68* (2013.01); *C07D 265/30* (2013.01); *C07D 403/12* (2013.01); *C07D 261/18* (2013.01); *C07D 213/56* (2013.01); *C07D 263/34* (2013.01); *C07D 213/61* (2013.01); *C07D 277/56* (2013.01); *C07C 2101/08* (2013.01); *C07D 333/38* (2013.01); *C07D 213/81* (2013.01); *C07D 241/24* (2013.01); *C07C 237/32* (2013.01); *C07D 241/12* (2013.01); *C07D 309/08* (2013.01); *C07D 231/14* (2013.01); *C07D 285/06* (2013.01); *C07D 295/125* (2013.01); *C07D 401/12* (2013.01); *C07C 2101/14* (2013.01)
USPC ............ 514/357; 544/405; 546/329; 549/510

(58) Field of Classification Search
CPC .......................... A61K 31/4418; C07D 213/24
USPC ............ 514/357; 544/405; 546/329; 549/510
See application file for complete search history.

*Primary Examiner* — Douglas M Willis
(74) *Attorney, Agent, or Firm* — Robert C. Hall

(57) ABSTRACT

Compounds of the formula I:

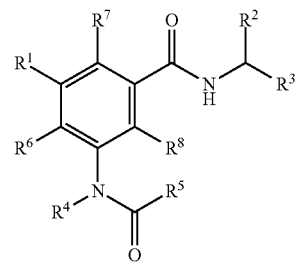

or a pharmaceutically acceptable salt thereof, wherein, $R^1$ is optionally substituted phenyl or optionally substituted pyridinyl, and $R^2$, $R^3$, $R^4$, $R^5$, $R^6$, $R^7$, $R^8$ and $R^9$ are as defined herein. Also disclosed are methods of using the compounds for treating diseases associated with $P2X_3$ and/or a $P2X_{2/3}$ receptor antagonists and methods of making the compounds.

16 Claims, No Drawings

PYRIDINYL AMIDES AS P2X3 AND P2X2/3 INHIBITORS

CROSS-REFERENCE TO RELATED APPLICATIONS

This application is a divisional application of U.S. Application Ser. No. 12/820,577 filed on Jun. 22, 2010 now U.S. Pat. No. 8,382,383, which is entitled to the benefit of U.S. provisional patent application Ser. No. 61/219,016 filed on Jun. 22, 2009, the disclosures of which are incorporated herein by reference.

FIELD OF THE INVENTION

This invention pertains to compounds useful for treatment of diseases associated with P2X purinergic receptors, and more particularly to $P2X_3$ and/or $P2X_{2/3}$ antagonists usable for treatment of genitourinary, pain, inflammatory, gastrointestinal and respiratory diseases, conditions and disorders.

BACKGROUND OF THE INVENTION

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, Burnstock (1993) Drug Dev. Res. 28:195-206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. Purinergic receptors, in particular, P2X receptors, are known to form homomultimers or heteromultimers. To date, cDNAs for several P2X receptors subtypes have been cloned, including: six homomeric receptors, $P2X_1$; $P2X_2$; $P2X_3$; $P2X_4$; $P2X_5$; and $P2X_7$; and several heteromeric receptors $P2X_{2/3}$, $P2X_{4/6}$, $P2X_{1/5}$ (See, e.g., Chen, et al. (1995) Nature 377:428-431; Lewis, et al. (1995) Nature 377:432-435; and Burnstock (1997) Neurophamacol. 36:1127-1139). The structure and chromosomal mapping of mouse genomic $P2X_3$ receptor subunit has also been described (Souslova, et al. (1997) Gene 195:101-111). In vitro, co-expression of $P2X_2$ and $P2X_3$ receptor subunits is necessary to produce ATP-gated currents with the properties seen in some sensory neurons (Lewis, et al. (1995) Nature 377:432-435).

P2X receptor subunits are found on afferents in rodent and human bladder urothelium. Data exists suggesting that ATP may be released from epithelial/endothelial cells of the urinary bladder or other hollow organs as a result of distention (Burnstock (1999) J. Anatomy 194:335-342; and Ferguson et al. (1997) J. Physiol. 505:503-511). ATP released in this manner may serve a role in conveying information to sensory neurons located in subepithelial components, e.g., suburothelial lamina propria (Namasivayam, et al. (1999) BJU Intl. 84:854-860). The P2X receptors have been studied in a number of neurons, including sensory, sympathetic, parasympathetic, mesenteric, and central neurons (Zhong, et al. (1998) Br. J. Pharmacol. 125:771-781). These studies indicate that purinergic receptors play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (Tsuda, et al. (1999) Br. J. Pharmacol. 128:1497-1504). ATP-induced activation of P2X receptors on dorsal root ganglion nerve terminals in the spinal cord has been shown to stimulate release of glutamate, a key neurotransmitter involved in nociceptive signaling (Gu and MacDermott, Nature 389:749-753 (1997)). $P2X_3$ receptors have been identified on nociceptive neurons in the tooth pulp (Cook et al., Nature 387:505-508 (1997)). ATP released from damaged cells may thus lead to pain by activating $P2X_3$ and/or $P2X_{2/3}$ containing receptors on nociceptive sensory nerve endings. This is consistent with the induction of pain by intradermally applied ATP in the human blister-base model (Bleehen, Br J Pharmacol 62:573-577 (1978)). P2X antagonists have been shown to be analgesic in animal models (Driessen and Starke, Naunyn Schmiedebergs Arch Pharmacol 350:618-625 (1994)). This evidence suggests that $P2X_2$ and $P2X_3$ are involved in nociception, and that modulators of P2X receptors are potentially useful as analgesics.

Other researchers have shown that $P2X_3$ receptors are expressed in human colon, and are expressed at higher levels in inflamed colon than in normal colon (Y. Yiangou et al, Neurogastroenterol Mot (2001) 13:365-69). Other researchers have implicated the $P2X_3$ receptor in detection of distension or intraluminal pressure in the intestine, and initiation of reflex contractions (X. Bian et al., J Physiol (2003) 551.1: 309-22), and have linked this to colitis (G. Wynn et al., Am J Physiol Gastrointest Liver Physiol (2004) 287:G647-57).

Inge Brouns et al. (Am J Respir Cell Mol Biol (2000) 23:52-61) found that $P2X_3$ receptors are expressed in pulmonary neuroepithelial bodies (NEBs), implicating the receptor in pain transmission in the lung. More recently, others have implicated $P2X_2$ and $P2X_3$ receptors in $pO_2$ detection in pulmonary NEBs (W. Rong et al., J Neurosci (2003) 23(36): 11315-21) and cough.

There is accordingly a need for compounds that act as modulators of P2X receptors, including antagonists of $P2X_3$ and $P2X_{2/3}$ receptors, as well as a need for methods of treating diseases, conditions and disorders mediated by $P2X_3$ and/or $P2X_{2/3}$ receptors. The present invention satisfies these needs as well as others.

SUMMARY OF THE INVENTION

The invention provides compounds of the formula I:

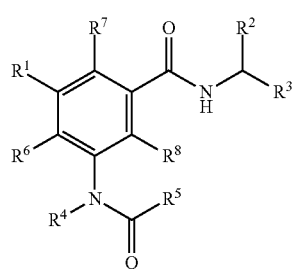

wherein:
R¹ is:
optionally substituted phenyl;
optionally substituted thienyl;
optionally substituted pyrimidinyl;
optionally substituted pyridazinyl; or
optionally substituted pyridinyl;
R² is:
hydrogen; or
$C_{1-6}$alkyl;
R³ is:
$C_{1-6}$alkyl;
hydroxy-$C_{1-6}$alkyl;
$C_{1-6}$alkoxy-$C_{1-6}$alkyl;
halo-$C_{1-6}$alkyl;
$C_{3-7}$cycloalkyl;
heteroaryl;
heterocyclyl;
heterocyclyl-$C_{1-6}$alkyl; or
$C_{3-7}$cycloalkyl-$C_{1-6}$alkyl;
or R² and R³ together form a $C_{3-7}$cycloalkyl;
R⁴ is:
hydrogen;
$C_{1-6}$alkyl;
$C_{3-7}$cycloalkyl;
$C_{3-7}$cycloalkyl-$C_{1-6}$alkyl; or
pyrimidinyl;
R⁵ is:
$C_{1-6}$alkyl;
$C_{1-6}$alkoxy;
$C_{3-7}$cycloalkyl;
$C_{1-6}$alkoxy-$C_{1-6}$alkyl;
amino-$C_{1-6}$alkyl;
oxetanyl optionally substituted once or twice with $C_{1-6}$alkyl;
phenyl optionally substituted once or twice with a group or groups independently selected from $C_{1-6}$alkyl, halo, halo-$C_{1-6}$alkyl and $C_{1-6}$alkoxy;
thienyl optionally substituted once or twice with a group or groups independently selected from $C_{1-6}$alkyl and $C_{1-6}$alkoxy;
furanyl optionally substituted once or twice with $C_{1-6}$alkyl;
thiazolyl optionally substituted once or twice with $C_{1-6}$alkyl;
oxazolyl optionally substituted once or twice with $C_{1-6}$alkyl;
isoxazolyl optionally substituted once or twice with a group or groups independently selected from $C_{1-6}$alkyl and phenyl;
pyrazolyl optionally substituted once or twice with $C_{1-6}$alkyl;
thiadiazolyl optionally substituted once with $C_{1-6}$alkyl;
tetrahydropyranyl;
morpholinyl;
piperidinyl optionally substituted with $C_{1-6}$alkyl or acetyl;
pyrimidinyl; or
pyridinyl optionally substituted once or twice with $C_{1-6}$alkyl; and
R⁶, R⁷ and R⁸ each independently is:
hydrogen; or
halo.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —SO₂— and R" is alkyl as defined herein.

"Alkylsulfonylalkyl means a moiety of the formula —R'—R"—R'''' where where R' is alkylene, R" is —SO₂— and R'''' is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted. In certain embodiments "aryl" means phenyl or naphthyl, each optionally substituted. In many embodiments "aryl" is optionally substituted phenyl.

"Arylalkyl" and "Aralkyl", which may be used interchangeably, mean a radical-$R^a R^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Cyanoalkyl"" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Urea" or "ureido" means a group of the formula —NR'—C(O)—NR"R"" wherein R', R" and R"" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R"" each independently is hydrogen or alkyl.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). In certain embodiments optional substituents for "aryl", phenyl", "heteroaryl" "cycloalkyl" or "heterocyclyl" include alkyl, halo, haloalkyl, alkoxy, cyano, amino and alkylsulfonyl. In many embodiments the substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Respiratory disorder" refers to, without limitation, chronic obstructive pulmonary disease (COPD), asthma, bronchospasm, and the like.

"Gastrointestinal disorder" ("GI disorder") refers to, without limitation, Irritable Bowel Syndrome (IBS), Inflammatory Bowel Disease (IBD), biliary colic and other biliary disorders, renal colic, diarrhea-dominant IBS, pain associated with GI distension, and the like.

"Pain" includes, without limitation, inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen sulfur or nitrogen atom in the structures herein indicates the presence of a hydrogen atom unless indicated otherwise. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure.

All patents and publications identified herein are incorporated herein by reference in their entirety.

Compounds of the Invention

The invention provides compounds of the formula I:

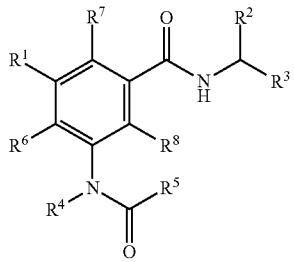

wherein:
R$^1$ is:
optionally substituted phenyl;
optionally substituted thienyl;
optionally substituted pyrimidinyl;
optionally substituted pyridazinyl; or
optionally substituted pyridinyl;
R$^2$ is:
hydrogen; or
C$_{1-6}$alkyl;
R$^3$ is:
C$_{1-6}$alkyl;
hydroxy-C$_{1-6}$alkyl;
C$_{1-6}$alkoxy-C$_{1-6}$alkyl;
halo-C$_{1-6}$alkyl;
C$_{3-7}$cycloalkyl;
heteroaryl;
heterocyclyl; or
C$_{3-7}$cycloalkyl-C$_{1-6}$alkyl;
or R$^2$ and R$^3$ together form a C$_{3-7}$cycloalkyl;
R$^4$ is:
hydrogen;
C$_{1-6}$alkyl;
C$_{3-7}$cycloalkyl;
C$_{3-7}$cycloalkyl-C$_{1-6}$alkyl; or
pyrimidinyl;
R$^5$ is:
C$_{1-6}$alkyl;
C$_{1-6}$alkoxy;
C$_{3-7}$cycloalkyl;
C$_{3-7}$cycloalkyl-C$_{1-6}$alkyl;
C$_{1-6}$alkoxy-C$_{1-6}$alkyl;
amino-C$_{1-6}$alkyl;
oxetanyl optionally substituted once or twice with C$_{1-6}$alkyl;
phenyl optionally substituted once or twice with a group or groups independently selected from C$_{1-6}$alkyl, halo, halo-C$_{1-6}$alkyl and C$_{1-6}$alkoxy;
thienyl optionally substituted once or twice with a group or groups independently selected from C$_{1-6}$alkyl and C$_{1-6}$alkoxy;
furanyl optionally substituted once or twice with C$_{1-6}$alkyl;
thiazolyl optionally substituted once or twice with C$_{1-6}$alkyl;
oxazolyl optionally substituted once or twice with C$_{1-6}$alkyl;
isoxazolyl optionally substituted once or twice with a group or groups independently selected from C$_{1-6}$alkyl and phenyl;
pyrazolyl optionally substituted once or twice with C$_{1-6}$alkyl;
thiadiazolyl optionally substituted once with C$_{1-6}$alkyl;
tetrahydropyranyl;
morpholinyl;
piperidinyl optionally substituted with C$_{1-6}$alkyl or acetyl; or
pyridinyl optionally substituted once or twice with C$_{1-6}$alkyl; and
R$^6$, R$^7$ and R$^8$ each independently is:
hydrogen; or
halo.

In certain embodiments of formula I, R$^1$ is phenyl substituted once or twice independently with halo or methyl.

In many embodiments of formula I, R$^1$ is phenyl substituted at the 4-position with methyl or halo and optionally substituted at the 2- and 6-positions with halo.

In many embodiments of formula I, R$^1$ is phenyl substituted at the 4-position with methyl or halo and optionally substituted at the 2-position with halo.

In certain embodiments of formula I, R$^1$ is 4-methyl-phenyl, 2-fluoro-4-methyl-phenyl, 2-chloro-4-fluoro-phenyl, 4-chloro-2-fluoro-phenyl, 2,4-dichloro-phenyl, 2,4-difluoro-phenyl, or 2-chloro-4-methyl-phenyl.

In certain embodiments of formula I, R$^1$ is 4-methyl-phenyl or 4-chloro-phenyl.

In certain embodiments of formula I, R$^1$ is 4-methyl-phenyl.

In certain embodiments of formula I, R$^1$ is 2-fluoro-4-methyl-phenyl.

In certain embodiments of formula I, R$^1$ is 2-chloro-4-fluoro-phenyl.

In certain embodiments of formula I, R$^1$ is 4-chloro-2-fluoro-phenyl.

In certain embodiments of formula I, R$^1$ is 2,4-dichloro-phenyl.

In certain embodiments of formula I, R$^1$ is 2,4-difluoro-phenyl.

In certain embodiments of formula I, R$^1$ is 2-chloro-4-methyl-phenyl.

In many embodiments of formula I, R$^1$ is optionally substituted pyridinyl. Exemplary pyridinyl include pyridin-2-yl, and pyridin-2-one-1-yl, each optionally substituted once, twice or three times with any of C$_{1-6}$alkyl, C$_{1-6}$alkyloxy, halo, C$_{1-6}$haloalkyl, C$_{1-6}$alkylsulfonyl or cyano. Preferred pyridyl include 4-methyl-pyridin-2-yl, 4-fluoro-pyridin-2-yl and 4-methyl-pyridin-2-one-1-yl.

In certain embodiments of formula I, R$^1$ is pyridin 2-yl substituted with methyl or halo at the 5-position.

In certain embodiments of formula I, R$^1$ is pyridin 2-yl substituted with methyl or halo at the 5-position and optionally substituted with halo at the 3-position.

In certain embodiments of formula I, R$^1$ is 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-pyridin-2-yl.

In certain embodiments of formula I, R$^1$ is 5-methyl-pyridin-2-yl.

In certain embodiments of formula I, R$^1$ is 5-chloro-pyridin-2-yl.

In certain embodiments of formula I, R$^1$ is 5-fluoro-pyridin-2-yl.

In certain embodiments of formula I, R$^1$ is 5-methyl-3-fluoro-pyridin-2-yl.

In certain embodiments of formula I, R$^1$ is 5-methyl-3-chloro-pyridin-2-yl.

In certain embodiments of formula I, R$^1$ is 3,5-difluoro-pyridin-2-yl.

In certain embodiments of formula I, $R^1$ is 3,5-dichloro-pyridin-2-yl.

In many embodiments of formula I, $R^7$, $R^8$ and $R^9$ are hydrogen.

In certain embodiments of formula I, one of $R^7$, $R^8$ and $R^9$ is halo and the others are hydrogen.

In certain embodiments of formula I, one of $R^7$, $R^8$ and $R^9$ is fluoro and the others are hydrogen.

In many embodiments the compounds of formula I may also be represented formula II:

wherein:
X is:
—N—; or
—CR$^a$; wherein R$^a$ is hydrogen, halo or methyl;
$R^{10}$ is;
methyl; or
halo; and
$R^2$, $R^3$, $R^4$ and $R^5$ are as defined herein.

In certain embodiments of formula I or formula II, $R^2$ is hydrogen.

In certain embodiments of formula I or formula II, $R^2$ is $C_{1-6}$alkyl.

In certain embodiments of formula I or formula II, $R^2$ is methyl.

In certain embodiments of formula I or formula II, $R^2$ and $R^3$ together form a $C_{3-7}$cycloalkyl.

In certain embodiments of formula I or formula II, $R^2$ and $R^3$ together form cyclopropyl.

In certain embodiments of formula I or formula II, $R^3$ is: $C_{1-6}$alkyl; $C_{1-6}$alkyloxy-$C_{1-6}$alkyl; hydroxy-$C_{1-6}$alkyl; $C_{1-6}$alkylsulfanyl-$C_{1-6}$alkyl; $C_{1-6}$alkylsulfonyl-$C_{1-6}$alkyl; amino-$C_{1-6}$alkyl; N—$C_6$alkyl-amino-$C_{1-6}$alkyl; N,N-di-$C_{1-6}$alkyl-amino-$C_{1-6}$alkyl; $C_{3-7}$cycloalkyl; optionally substituted phenyl; heteroaryl, or heterocyclyl-$C_{1-6}$alkyl.

In certain embodiments of formula I or formula II, $R^3$ is: $C_{1-6}$alkyloxy-$C_{1-6}$alkyl; hydroxy-$C_{1-6}$alkyl; heteroaryl, or heterocyclyl-$C_{1-6}$alkyl.

In certain embodiments of formula I or formula II, $R^3$ is $C_{1-6}$alkyloxy-$C_{1-6}$alkyl. One preferred $C_{1-6}$alkyloxy-$C_{1-6}$ alkyl is methoxymethyl.

In certain embodiments of formula I or formula II, $R^3$ is hydroxy-$C_{1-6}$alkyl. One preferred hydroxy-$C_{1-6}$alkyl is hydroxymethyl.

In certain embodiments of formula I or formula II, $R^3$ is heteroaryl.

In certain embodiments where $R^3$ is heteroaryl, such heteroaryl may be pyridinyl, pyrimidinyl, pyrazinyl, pyridazinyl, pyrazolyl, imidazolyl, thienyl, thiazolyl, oxazolyl, isoxazolyl, triazolyl, oxadiazolyl, 3-oxo-2,3-dihydro-isoxazolyl, tetrazolyl, imidazo[2,1-b]thiazolyl, imidazo[1,2-a]pyridinyl, imidazo[4,5-b]pyridinyl, and benzimidazolyl, each of which may be optionally substituted one, two or three times with a group or groups independently selected from $C_{1-6}$alkyl, $C_{1-6}$alkoxy, $C_{1-6}$alkoxy-$C_{1-6}$alkyl, halo-$C_{1-6}$alkyl, halo, amino, N—$C_{1-6}$alkyl-amino, or N,N-di-($C_{1-6}$alkyl)-amino. More preferably, such heteroarly may be optionally substituted once or twice with a group or groups independently selected from methyl, ethyl, n-propyl, fluoro, chloro, trifluoromethyl, amino, methylamino or dimethylamino.

In certain embodiments where $R^3$ is heteroaryl, such heteroaryl may be pyridinyl, pyrimidinyl, pyrazinyl, pyridazinyl, pyrazolyl or thiazolyl, each of which may be optionally substituted once or twice with a group or groups independently selected from methyl, ethyl, n-propyl, fluoro, chloro, amino, methylamino or dimethylamino.

In certain embodiments where $R^3$ heteroaryl, such heteroaryl may be pyridinyl, pyrimidinyl, or pyrazinyl, each of which may be optionally substituted once or twice with a group or groups independently selected from methyl, fluoro, chloro, amino, methylamino or dimethylamino.

In certain embodiments where $R^3$ heteroaryl, such heteroaryl may be pyridinyl, pyrimidinyl, or pyrazinyl, each of which may be optionally substituted once or twice with methyl.

In certain embodiments where $R^3$ heteroaryl, such heteroaryl may be pyrimidinyl or pyrazinyl, each of which may be optionally substituted once or twice with methyl.

In certain embodiments where $R^3$ heteroaryl, such heteroaryl may be pyrazinyl optionally substituted once or twice with methyl.

In certain embodiments of formula I or formula II, where $R^3$ is heteroaryl, such heteroaryl may be thiophen-2-yl, pyridin-2-yl, pyridin-3-yl, pyridin-4-yl, oxazol-2-yl, pyrimidin-2-yl, pyridazin-4-yl, pyrazin-2-yl, 5-methyl-pyrazin-2-yl, imidazol-1-yl, pyrazol-1-yl, 3,5-dimethyl-pyrazol-1-yl, 2-methyl-thiazol-4-yl, 3-(2-chloro-phenyl)-[1,2,4]-oxadiazol-5-yl, 3-(pyridin-4-yl)-[1,2,4]-oxadiazol-5-yl, pyridazin-3-yl, 2-methyl-pyrazol-3-yl, thiazol-5-yl, 1-methyl-imidazol-2-yl, 6-chloro-pyrimidin-4-yl, 4-ethyl-[1,2,4]-triazol-3-yl, 1,3,5-trimethyl-pyrazol-4-yl, 1,5-dimethyl-pyrazol-4-yl, 1,3-dimethyl-pyrazol-4-yl, 3-(2-methoxy-ethyl)-[1,2,4]-oxadiazol-5-yl, 3-(pyridin-3-yl-[1,2,4]-oxadiazol-5-yl, tetrazol-5-yl, pyrazol-3-yl, 4-amino-2-methyl-pyrimidin-5-yl, 2-amino-pyrimidin-4-yl, 6-methoxy-pyridazin-3-yl, 3-oxo-2,3-dihydro-isoxazol-5-yl, 3-methyl-thiophen-2-yl, 5-methyl-[1,3,4]-oxadiazol-2-yl, 4-methyl-isoxazol-3-yl, 3-trifluoromethyl-pyrazol-1-yl, 1-methyl-pyrazol-3-yl, 3-methyl-pyrazol-1-yl, 5-methyl-3-trifluoromethyl-pyrazol-1-yl, 5-cyclopropyl-3-trifluoromethyl-pyrazol-1-yl, imidazo[2,1-b]-thiazol-6-yl, thiazol-4-yl, 2-propyl-pyrazol-3-yl, 2-ethyl-pyrazol-3-yl, 5-amino-pyridazin-2-yl, 3-amino-pyridazin-2-yl, 3-chloro-pyridazin-2-yl, 2-amino-pyrimidin-5-yl, 1-methyl-imidazol-4-yl, 6-amino-pyridin-3-yl, 6-amino-pyridazin-2-yl, 2-amino-pyridin-4-yl, 2-dimethylamino-pyrimidin-5-yl, 6-amino-pyridin-2-yl, 2-methylamino-pyridin-4-yl, 2-dimethylamino-pyridin-4-yl, 3-methyl-2-dimethylamino-pyridin-4-yl, pyrimidin-5-yl, 2-methyl-pyridin-4-yl, 6-methylamino-pyridin-3-yl, 6-dimethylamino-pyridin-3-yl, 6-methylamino-pyrimidin-4-yl, 6-dimethylamino-pyridin-3-yl, 6-methylamino-pyridin-3-yl, 2-methylamino-pyrimidin-5-yl, 6-methyl-pyridin-3-yl, 4-methyl-thiazol-2-yl, 2,6-dimethyl-pyridin-3-yl, imidazo[1,2-a]pyridin-2-yl, 6-methyl-pyridin-2-yl, 1-ethyl-pyrazol-3-yl, 3-methyl-pyridin-2-yl, 4-methyl-thiazol-5-yl, 1-ethyl-imidazol-2-yl, 1-methyl-pyrazol-4-yl, imidazo[4,5-b]pyridin-2-yl, 3,5-difluoro-pyridin-2-yl, 6-fluoro-pyridin-2-yl, 1,5-dimethyl-pyrazol-3-yl, 5-methyl-pyridin-2-yl, 6-trifluoromethyl-pyridin-3-yl, 5-methyl-isoxazol-3-yl, 5-methyl-imidazol-2-yl, 5-methoxy-benzimidazol-2-yl,

[1,2,4]triazol-3-yl, 6-methyl-pyridazin-3-yl, 1-methyl-6-oxo-1,6-dihydro-pyridin-3-yl or 8-methyl-imidazo[1,2-a]pyridin-2-yl.

In certain embodiments of formula I or formula II, $R^3$ is heterocyclyl-$C_{1-6}$alkyl.

In embodiments where $R^3$ is heterocyclyl-$C_{1-6}$alkyl, such heterocyclyl-$C_{1-6}$alkyl may be heterocyclyl-methyl such as morpholinomethyl, piperidinyl-methyl, piperazinyl-methyl, thiomorpholinylmethyl, pyrrolidinylmethyl, or azetidinylmethyl, the heterocyclyl portion of each of which may be optionally substituted once or twice with a group or groups independently selected from methyl, methoxy, halo, methanesulfonyl, oxo or acetyl.

In embodiments where $R^3$ is heterocyclyl-methyl, such heterocyclylmethyl may be morpholin-4-yl-methyl, 4-methanesulfonyl-piperazin-1-yl-methyl, 4-acetyl-piperazin-1-yl-methyl, piperidin-1-yl, thiomorpholin-4-yl-methyl, 4-methyl-piperazin-1-yl-methyl, 3-oxo-piperazin-1-yl-methyl, 3-methoxy-piperidin-1-yl-methyl, 4-methoxy-piperidin-1-yl-methyl, 4-hydroxy-piperidin-1-yl-methyl, 1-oxo-thiomorpholin-4-yl-methyl, 3-hydroxy-pyrrolidin-1-yl-methyl, azetidin-3-yl-methyl, 4-methanesulfonyl-piperidin-1-yl-methyl, 4-fluoro-piperidin1-yl-methyl, 4-acetyl-3-methyl-piperazin-1-yl-methyl, 4-acetyl-3,5-dimethyl-piperazin-1-yl-methyl, 2,6-dimethyl-morpholin-4-yl-methyl, 4,4-difluoro-piperidin1-yl-methyl, 3-fluoro-piperidin1-yl-methyl, 4-methyl-4-hydroxy-piperidin1-yl-methyl, or 3-fluoro-4-methoxy-piperidin1-yl-methyl.

In certain embodiments of formula I or formula II, $R^3$ is hydroxymethyl, methoxymethyl, or pyrazin-2-yl.

In certain embodiments of formula I or formula II, $R^3$ is hydroxymethyl, methoxymethyl, pyrazin-2-yl or morpholin-4-yl-methyl.

In certain embodiments of formula I or formula II, $R^3$ is hydroxymethyl, methoxymethyl, pyrazin-2-yl or 5-methyl-pyrazin-2-yl.

In certain embodiments of formula I or formula II, $R^3$ is hydroxymethyl, methoxymethyl, pyrazin-2-yl, 5-methyl-pyrazin-2-yl, 6-methyl-pyridazin-3-yl, or 1-methyl-6-oxo-1,6-dihydro-pyridin-3-yl.

In certain embodiments of formula I or formula II, $R^3$ is hydroxymethyl, methoxymethyl, 5-methyl-pyrazin-2-yl, 2-methyl-pyrimidin-5-yl, 5-methyl-pyrimidin-2-yl, hydroxymethyl or methoxymethyl.

In certain embodiments of formula I or formula II, $R^3$ is hydroxymethyl.

In certain embodiments of formula I or formula II, $R^3$ is methoxymethyl.

In certain embodiments of formula I or formula II, $R^3$ is pyrazin-2-yl.

In certain embodiments of formula I or formula II, $R^3$ is 5-methyl-pyrazin-2-yl.

In certain embodiments of formula I or formula II, $R^3$ is morpholin-4-ylmethyl.

In certain embodiments of formula I or formula II, $R^3$ is 1-methyl-6-oxo-1,6-dihydro-pyridin-3-yl.

In certain embodiments of formula I or formula II, $R^3$ is 2-methyl-pyrimidin-5-yl In certain embodiments of formula I or formula II, $R^3$ is 6-methyl-pyridazin-3-yl.

In certain embodiments of formula I or formula II, $R^4$ is hydrogen.

In certain embodiments of formula I or formula II, $R^4$ is $C_{1-6}$alkyl.

In certain embodiments of formula I or formula II, $R^4$ is $C_{3-7}$cycloalkyl.

In certain embodiments of formula I or formula II, $R^4$ is $C_{3-7}$cycloalkyl-$C_{1-6}$alkyl.

In certain embodiments of formula I or formula II, $R^4$ is pyrimidinyl.

In certain embodiments of formula I or formula II, $R^4$ is methyl.

In certain embodiments of formula I or formula II, $R^4$ is ethyl.

In certain embodiments of formula I or formula II, $R^4$ is hydrogen, methyl, ethyl or pyrimidin-4-yl.

In certain embodiments of formula I or formula II, $R^4$ is hydrogen, methyl or ethyl.

In certain embodiments of formula I or formula II, $R^4$ is methyl or ethyl.

In certain embodiments of formula I or formula II, $R^5$ is $C_{1-6}$alkyl.

In certain embodiments of formula I or formula II, $R^5$ is $C_{1-6}$alkoxy.

In certain embodiments of formula I or formula II, $R^5$ is $C_{3-7}$cycloalkyl.

In certain embodiments of formula I or formula II, $R^5$ is oxetanyl optionally substituted once or twice with $C_{1-6}$alkyl.

In certain embodiments of formula I or formula II, $R^5$ is $C_{1-6}$alkoxy-$C_{1-6}$alkyl.

In certain embodiments of formula I or formula II, $R^5$ is $C_{3-7}$cycloalkyl-$C_{1-6}$alkyl.

In certain embodiments of formula I or formula II, $R^5$ is phenyl optionally substituted once or twice with a group or groups independently selected from $C_{1-6}$alkyl, halo, halo-$C_{1-6}$alkyl and $C_{1-6}$alkoxy.

In certain embodiments of formula I or formula II, $R^5$ is thienyl optionally substituted once or twice with a group or groups independently selected from $C_{1-6}$alkyl and $C_{1-6}$alkoxy.

In certain embodiments of formula I or formula II, $R^5$ is furanyl optionally substituted once or twice with $C_{1-6}$alkyl.

In certain embodiments of formula I or formula II, $R^5$ is thiazolyl optionally substituted once or twice with $C_{1-6}$alkyl.

In certain embodiments of formula I or formula II, $R^5$ is oxazolyl optionally substituted once or twice with $C_{1-6}$alkyl.

In certain embodiments of formula I or formula II, $R^5$ is isoxazolyl optionally substituted once or twice with a group or groups independently selected from $C_{1-6}$alkyl and phenyl.

In certain embodiments of formula I or formula II, $R^5$ is pyrazolyl optionally substituted once or twice with $C_{1-6}$alkyl.

In certain embodiments of formula I or formula II, $R^5$ is thiadiazolyl optionally substituted once with $C_{1-6}$alkyl.

In certain embodiments of formula I or formula II, $R^5$ is tetrahydropyranyl.

In certain embodiments of formula I or formula II, $R^5$ is morpholinyl.

In certain embodiments of formula I or formula II, $R^5$ is piperidinyl optionally substituted with $C_{1-6}$alkyl or acetyl.

In certain embodiments of formula I or formula II, $R^5$ is pyridinyl optionally substituted once or twice with $C_{1-6}$alkyl.

In certain embodiments of formula I or formula II, $R^5$ is $C_{1-6}$alkyl, $C_{3-7}$cycloalkyl or $C_{3-7}$cycloalkyl-$C_{1-6}$alkyl.

In certain embodiments of formula I or formula II, $R^5$ is $C_{1-6}$alkyl or $C_{3-7}$cycloalkyl.

In certain embodiments of formula I or formula II, $R^5$ is $C_{3-5}$-branched alkyl such as isopropyl, isobutyl, tert butyl and the like.

In certain embodiments of formula I or formula II, $R^5$ is methyl, ethyl, isopropyl, isobutyl, or tert butyl.

In certain embodiments of formula I or formula II, $R^5$ is isopropyl, isobutyl or tert butyl.

In certain embodiments of formula I or formula II, $R^5$ is isopropyl.

In certain embodiments of formula I or formula II, $R^5$ is isobutyl.

In certain embodiments of formula I or formula II, $R^5$ is tert butyl.

In certain embodiments of formula II, $R^{10}$ is methyl.

In certain embodiments of formula II, $R^{10}$ is halo.

In certain embodiments of formula II, X is N.

In certain embodiments of formula II, X is $CR^a$.

In certain embodiments of formula II, X is $CR^a$ and $R^a$ is hydrogen or halo.

In certain embodiments of formula II, X is CH.

Where any of $R^1, R^2, R^3, R^4, R^5, R^6, R^7, R^8, R^9, R^{10}$ and $R^a$ is alkyl or contains an alkyl moiety, such alkyl is preferably lower alkyl, i.e. $C_1$-$C_6$alkyl, and more preferably $C_1$-$C_4$alkyl.

The invention also provides methods for treating a disease or condition mediated by or otherwise associated with a $P2X_3$ receptor antagonist, a $P2X_{2/3}$ receptor antagonist, or both, the method comprising administering to a subject in need thereof an effective amount of a compound of the invention.

The disease may be genitorurinary disease or urinary tract disease. In other instances the disease may be a disease is associated with pain. The urinary tract disease may be: reduced bladder capacity; frequency micturition; urge incontinence; stress incontinence; bladder hyperreactivity; benign prostatic hypertrophy; prostatitis; detrusor hyperreflexia; urinary frequency; nocturia; urinary urgency; overactive bladder; pelvic hypersensitivity; urethritis; prostatitits; pelvic pain syndrome; prostatodynia; cystitis; or idiophatic bladder hypersensitivity.

The disease associated with pain may be: inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

The disease may be a respiratory disorder, such as chronic obstructive pulmonary disorder (COPD), asthma, or bronchospasm, or a gastrointestinal (GI) disorder such as Irritable Bowel Syndrome (IBS), Inflammatory Bowel Disease (IBD), biliary colic and other biliary disorders, renal colic, diarrhea-dominant IBS, pain associated with GI distension.

Representative compounds in accordance with the methods of the invention are shown in Table 1, with $pIC_{50}$ values for the $P2X_3$ receptor.

TABLE 1

| # | Structure | Name | $P2X_3$ |
|---|---|---|---|
| 1 | 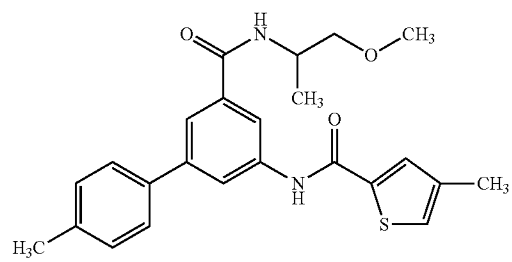 | 4-Methyl-thiophene-2-carboxylic acid [5-(2-methoxy-1-methyl-ethylcarbamoyl)-4'-methyl-biphenyl-3-yl]-amide | 6.31 |
| 2 | 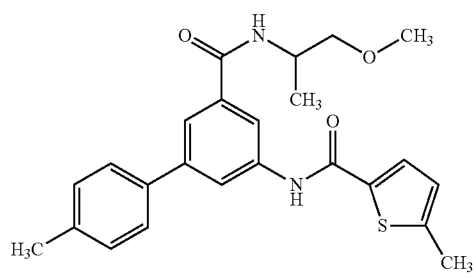 | 5-Methyl-thiophene-2-carboxylic acid [5-(2-methoxy-1-methyl-ethylcarbamoyl)-4'-methyl-biphenyl-3-yl]-amide | 5.2 |
| 3 | 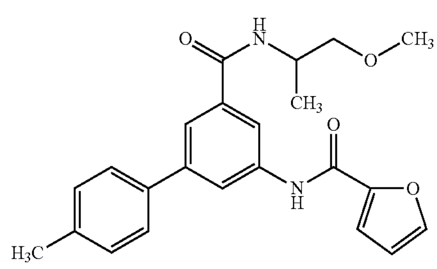 [SMILES: COCC(C)NC(=O)c1cc(NC(=O)c2ccco2)cc(-c2ccc(C)cc2)c1] | Furan-2-carboxylic acid [5-(2-methoxy-1-methyl-ethylcarbamoyl)-4'-methyl-biphenyl-3-yl]-amide | 5.66 |

TABLE 1-continued

| # | Structure | Name | P2X$_3$ |
|---|---|---|---|
| 4 | 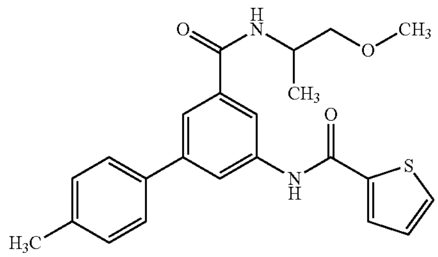 [SMILES: COCC(C)NC(=O)c1cc(NC(=O)c2cccs2)cc(-c2ccc(C)cc2)c1] | Thiophene-2-carboxylic acid [5-(2-methoxy-1-methyl-ethylcarbamoyl)-4'-methyl-biphenyl-3-yl]-amide | 5.51 |
| 5 | 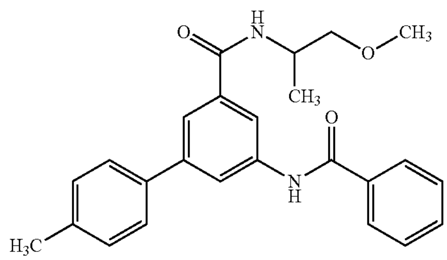 | 5-Benzoylamino-4'-methyl-biphenyl-3-carboxylic acid (2-methoxy-1-methyl-ethyl)-amide | 5.69 |
| 6 | 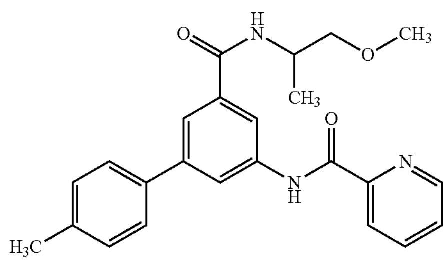 [SMILES: COCC(C)NC(=O)c1cc(NC(=O)c2ccccc2)cc(-c2ccc(C)cc2)c1] | Pyridine-2-carboxylic acid [5-(2-methoxy-1-methyl-ethylcarbamoyl)-4'-methyl-biphenyl-3-yl]-amide | 5.62 |
| 7 | 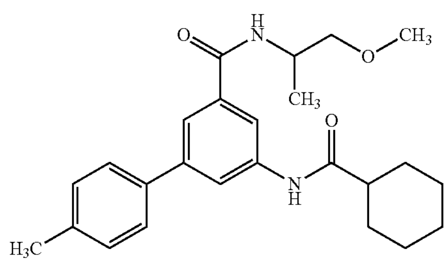 [SMILES: COCC(C)NC(=O)c1cc(NC(=O)C2CCCCC2)cc(-c2ccc(C)cc2)c1] | 5-(Cyclohexanecarbonyl-amino)-4'-methyl-biphenyl-3-carboxylic acid (2-methoxy-1-methyl-ethyl)-amide | 5.49 |
| 8 | 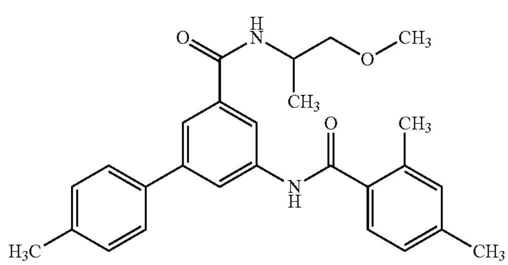 | 5-(2,4-Dimethyl-benzoylamino)-4'-methyl-biphenyl-3-carboxylic acid (2-methoxy-1-methyl-ethyl)-amide | 5.35 |
| 9 | 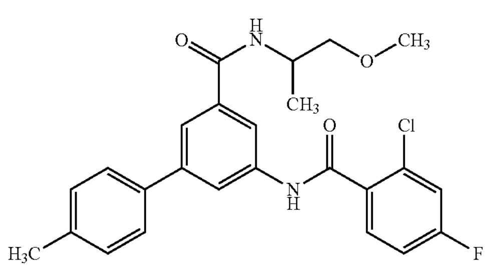 [SMILES: COCC(C)NC(=O)c1cc(NC(=O)c2ccc(F)cc2Cl)cc(-c2ccc(C)cc2)c1] | 5-(2-Chloro-4-fluoro-benzoylamino)-4'-methyl-biphenyl-3-carboxylic acid (2-methoxy-1-methyl-ethyl)-amide | 5.44 |

TABLE 1-continued

| # | Structure | Name | P2X$_3$ |
|---|---|---|---|
| 10 | 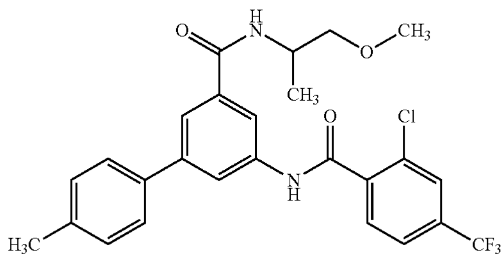 [SMILES: COCC(C)NC(=O)c1cc(NC(=O)c2ccc(C(F)(F)F)cc2Cl)cc(-c2ccc(C)cc2)c1] | 5-(2-Chloro-4-trifluoromethyl-benzoylamino)-4'-methyl-biphenyl-3-carboxylic acid (2-methoxy-1-methyl-ethyl)-amide | 5.87 |
| 11 | 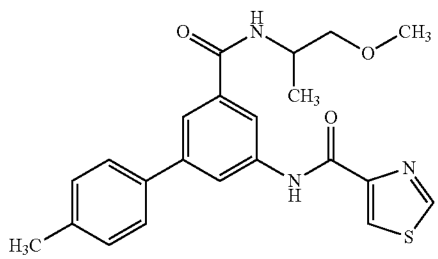 [SMILES: COCC(C)NC(=O)c1cc(NC(=O)c2cscn2)cc(-c2ccc(C)cc2)c1] | Thiazole-4-carboxylic acid [5-(2-methoxy-1-methyl-ethylcarbamoyl)-4'-methyl-biphenyl-3-yl]-amide | 5.56 |
| 12 | 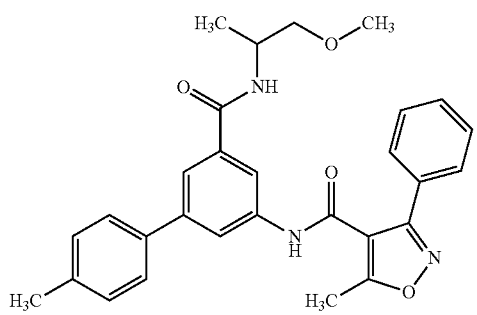 [SMILES: COCC(C)NC(=O)c1cc(NC(=O)c2c(-c3ccccc3)noc2C)cc(-c2ccc(C)cc2)c1] | 5-Methyl-3-phenyl-isoxazole-4-carboxylic acid [5-(2-methoxy-1-methyl-ethylcarbamoyl)-4'-methyl-biphenyl-3-yl]-amide | 5.59 |
| 13 | 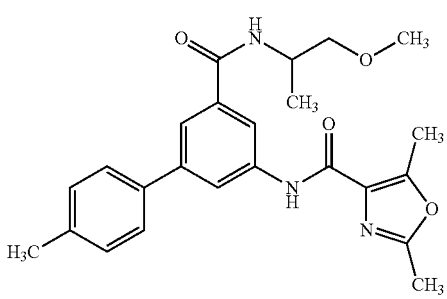 [SMILES: COCC(C)NC(=O)c1cc(NC(=O)c2nc(C)oc2C)cc(-c2ccc(C)cc2)c1] | 2,5-Dimethyl-oxazole-4-carboxylic acid [5-(2-methoxy-1-methyl-ethylcarbamoyl)-4'-methyl-biphenyl-3-yl]-amide | 5.93 |
| 14 | 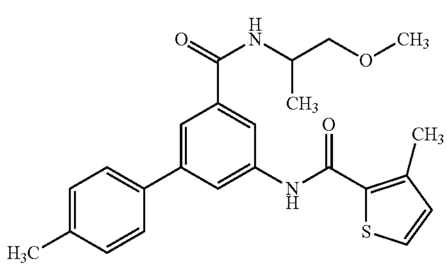 [SMILES: COCC(C)NC(=O)c1cc(NC(=O)c2sccc2C)cc(-c2ccc(C)cc2)c1] | 3-Methyl-thiophene-2-carboxylic acid [5-(2-methoxy-1-methyl-ethylcarbamoyl)-4'-methyl-biphenyl-3-yl]-amide | 5.35 |

TABLE 1-continued

| # | Structure | Name | P2X$_3$ |
|---|---|---|---|
| 15 | 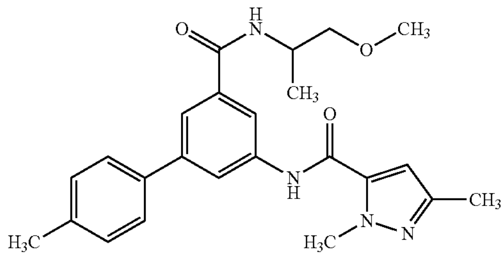 | 2,5-Dimethyl-2H-pyrazole-3-carboxylic acid [5-(2-methoxy-1-methyl-ethylcarbamoyl)-4'-methyl-biphenyl-3-yl]-amide | 5.34 |
| 16 | 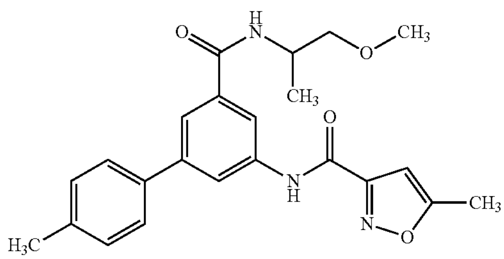 | 5-Methyl-isoxazole-3-carboxylic acid [5-(2-methoxy-1-methyl-ethylcarbamoyl)-4'-methyl-biphenyl-3-yl]-amide | 5.4 |
| 17 | 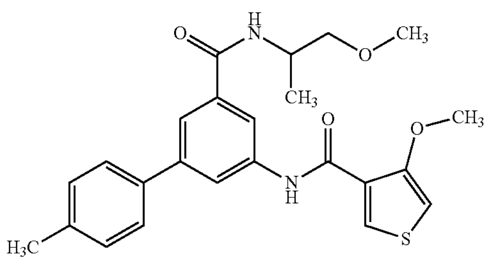 | 4-Methoxy-thiophene-3-carboxylic acid [5-(2-methoxy-1-methyl-ethylcarbamoyl)-4'-methyl-biphenyl-3-yl]-amide | 5.87 |
| 18 | 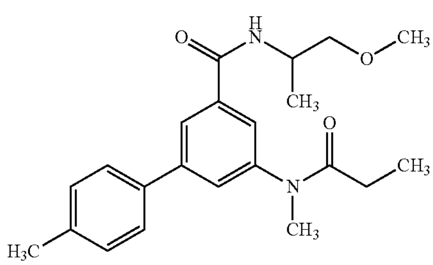 [SMILES: CCC(=O)N(C)c1cc(C(=O)NC(C)COC)cc(-c2ccc(C)cc2)c1] | 4'-Methyl-5-(methyl-propionyl-amino)-biphenyl-3-carboxylic acid (2-methoxy-1-methyl-ethyl)-amide | 5.35 |
| 19 | 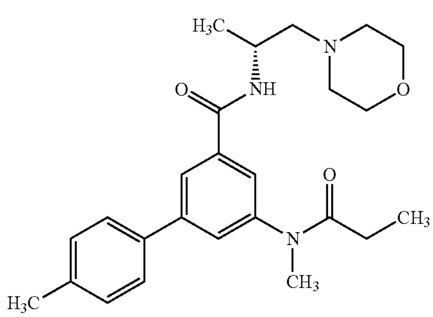 [SMILES: CCC(=O)N(C)c1cc(C(=O)N[C@H](C)CN2CCOCC2)cc(-c2ccc(C)cc2)c1] | 4'-Methyl-5-(methyl-propionyl-amino)-biphenyl-3-carboxylic acid ((R)-1-methyl-2-morpholin-4-yl-ethyl)-amide | 6.88 |

TABLE 1-continued

| # | Structure | Name | P2X$_3$ |
|---|---|---|---|
| 20 | 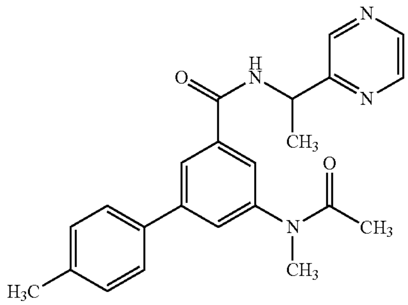 [SMILES: CC(=O)N(C)c1cc(C(=O)NC(C)c2cnccn2)cc(-c2ccc(C)cc2)c1] | 5-(Acetyl-methyl-amino)-4'-methyl-biphenyl-3-carboxylic acid (1-pyrazin-2-yl-ethyl)-amide | 6.05 |
| 21 | 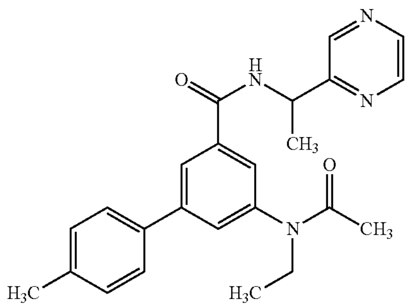 [SMILES: CCN(C(C)=O)c1cc(C(=O)NC(C)c2cnccn2)cc(-c2ccc(C)cc2)c1] | 5-(Acetyl-ethyl-amino)-4'-methyl-biphenyl-3-carboxylic acid (1-pyrazin-2-yl-ethyl)-amide | 7.28 |
| 22 | 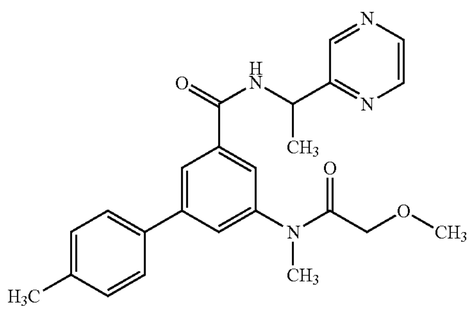 | 5-[(2-Methoxy-acetyl)-methyl-amino]-4'-methyl-biphenyl-3-carboxylic acid (1-pyrazin-2-yl-ethyl)-amide | 6.69 |
| 23 | 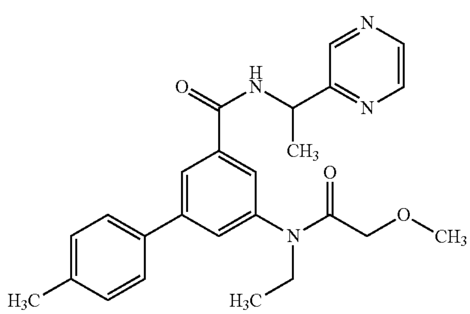 | 5-[Ethyl-(2-methoxy-acetyl)-amino]-4'-methyl-biphenyl-3-carboxylic acid (1-pyrazin-2-yl-ethyl)-amide | 6.5 |
| 24 | 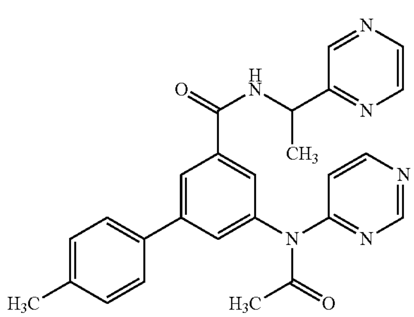 [SMILES: CC(=O)N(c1cc(C(=O)NC(C)c2cnccn2)cc(-c2ccc(C)cc2)c1)c1ccncn1] | 5-(Acetyl-pyrimidin-4-yl-amino)-4'-methyl-biphenyl-3-carboxylic acid (1-pyrazin-2-yl-ethyl)-amide | 6.31 |

TABLE 1-continued

| # | Structure | Name | P2X$_3$ |
|---|---|---|---|
| 25 | 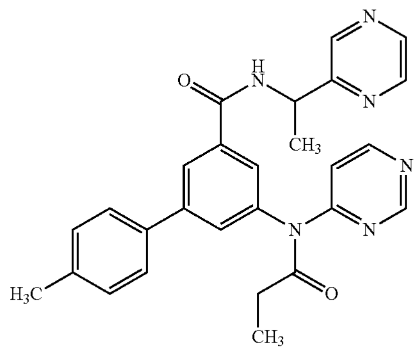 [SMILES: CCC(=O)N(c1cc(C(=O)NC(C)c2cnccn2)cc(-c2ccc(C)cc2)c1)c1ccncn1] | 4'-Methyl-5-(propionyl-pyrimidin-4-yl-amino)-biphenyl-3-carboxylic acid (1-pyrazin-2-yl-ethyl)-amide | 6.16 |
| 26 | 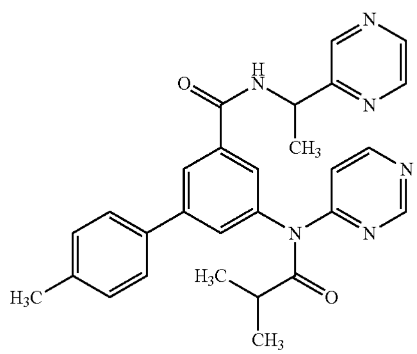 [SMILES: Cc1ccc(-c2cc(C(=O)NC(C)c3cnccn3)cc(N(C(=O)C(C)C)c3ccncn3)c2)cc1] | 5-(Isobutyryl-pyrimidin-4-yl-amino)-4'-methyl-biphenyl-3-carboxylic acid (1-pyrazin-2-yl-ethyl)-amide | 6.99 |
| 27 | 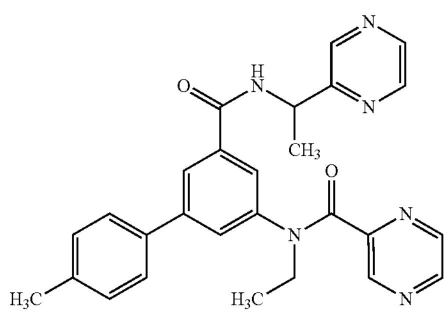 [SMILES: CCN(C(=O)c1cnccn1)c1cc(C(=O)NC(C)c2cnccn2)cc(-c2ccc(C)cc2)c1] | Pyrazine-2-carboxylic acid ethyl-[4'-methyl-5-(1-pyrazin-2-yl-ethylcarbamoyl)-biphenyl-3-yl]-amide | 5.35 |
| 28 | 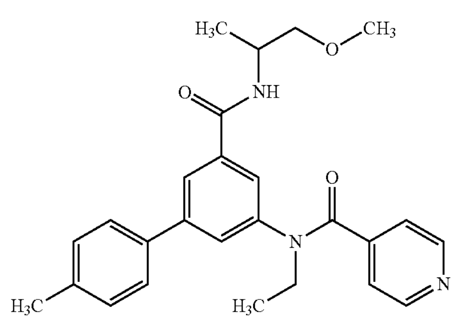 [SMILES: CCN(C(=O)c1ccncc1)c1cc(C(=O)NC(C)COC)cc(-c2ccc(C)cc2)c1] | N-Ethyl-N-[5-(2-methoxy-1-methyl-ethylcarbamoyl)-4'-methyl-biphenyl-3-yl]-isonicotinamide | 5.4 |

TABLE 1-continued

| # | Structure | Name | P2X$_3$ |
|---|---|---|---|
| 29 | 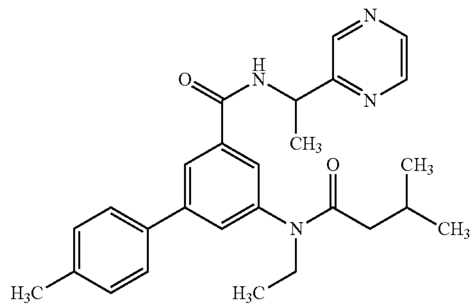 | 5-[Ethyl-(3-methyl-butyryl)-amino]-4'-methyl-biphenyl-3-carboxylic acid (1-pyrazin-2-yl-ethyl)-amide | 7.38 |
| 30 | 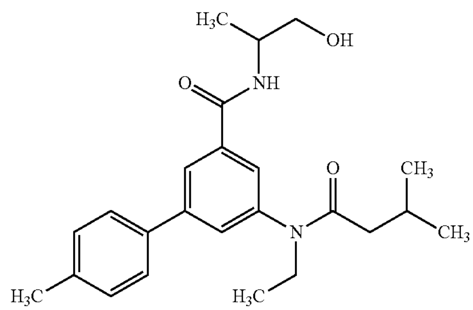 [SMILES: CCN(C(=O)CC(C)C)c1cc(C(=O)NC(C)CO)cc(-c2ccc(C)cc2)c1] | 5-[Ethyl-(3-methyl-butyryl)-amino]-4'-methyl-biphenyl-3-carboxylic acid (2-hydroxy-1-methyl-ethyl)-amide | 7.33 |
| 31 | 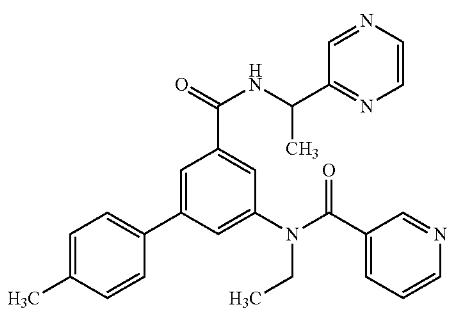 [SMILES: CCN(C(=O)c1cccnc1)c1cc(C(=O)NC(C)c2cnccn2)cc(-c2ccc(C)cc2)c1] | N-Ethyl-N-[4'-methyl-5-(1-pyrazin-2-yl-ethylcarbamoyl)-biphenyl-3-yl]-nicotinamide | 5.91 |
| 32 | 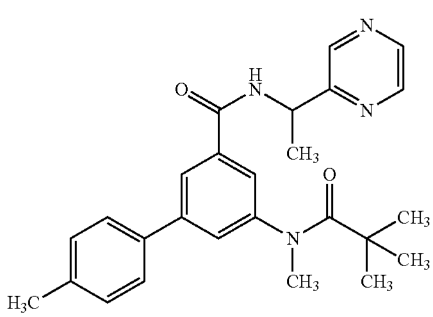 [SMILES: Cc1ccc(-c2cc(C(=O)NC(C)c3cnccn3)cc(N(C)C(=O)C(C)(C)C)c2)cc1] | 5-[(2,2-Dimethyl-propionyl)-methyl-amino]-4'-methyl-biphenyl-3-carboxylic acid (1-pyrazin-2-yl-ethyl)-amide | 8.01 |
| 33 | 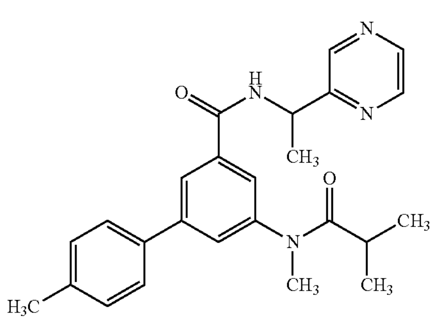 [SMILES: Cc1ccc(-c2cc(C(=O)NC(C)c3cnccn3)cc(N(C)C(=O)C(C)C)c2)cc1] | 5-(Isobutyryl-methyl-amino)-4'-methyl-biphenyl-3-carboxylic acid (1-pyrazin-2-yl-ethyl)-amide | 8.3 |

TABLE 1-continued

| # | Structure | Name | P2X$_3$ |
|---|---|---|---|
| 34 | 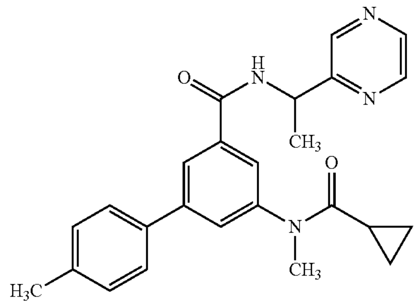 [SMILES: Cc1ccc(-c2cc(C(=O)NC(C)c3cnccn3)cc(N(C)C(=O)C3CC3)c2)cc1] | 5-(Cyclopropanecarbonyl-methyl-amino)-4'-methyl-biphenyl-3-carboxylic acid (1-pyrazin-2-yl-ethyl)-amide | 7.97 |
| 35 | 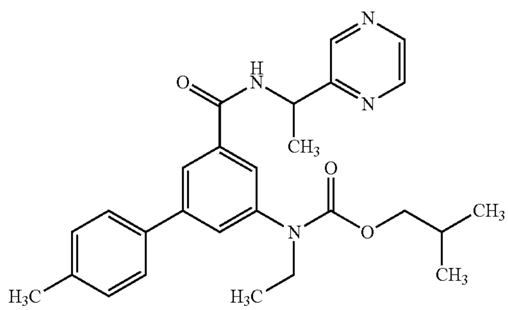 [SMILES: CCN(C(=O)OCC(C)C)c1cc(C(=O)NC(C)c2cnccn2)cc(-c2ccc(C)cc2)c1] | Ethyl-[4'-methyl-5-(1-pyrazin-2-yl-ethylcarbamoyl)-biphenyl-3-yl]-carbamic acid isobutyl ester | 6.82 |
| 36 | 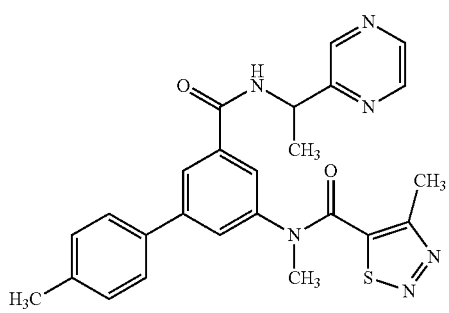 [SMILES: Cc1ccc(-c2cc(C(=O)NC(C)c3cnccn3)cc(N(C)C(=O)c3snnc3C)c2)cc1] | 4-Methyl-[1,2,3]thiadiazole-5-carboxylic acid methyl-[4'-methyl-5-(1-pyrazin-2-yl-ethylcarbamoyl)-biphenyl-3-yl]-amide | 5.3 |
| 37 | 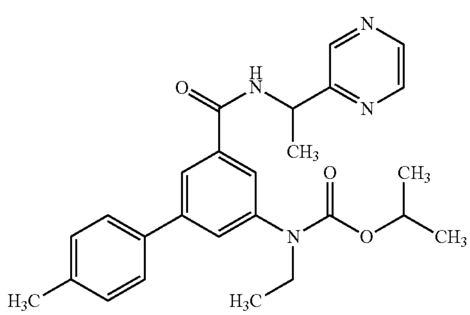 [SMILES: CCN(C(=O)OC(C)C)c1cc(C(=O)NC(C)c2cnccn2)cc(-c2ccc(C)cc2)c1] | Ethyl-[4'-methyl-5-(1-pyrazin-2-yl-ethylcarbamoyl)-biphenyl-3-yl]-carbamic acid isopropyl ester | 7.12 |
| 38 | 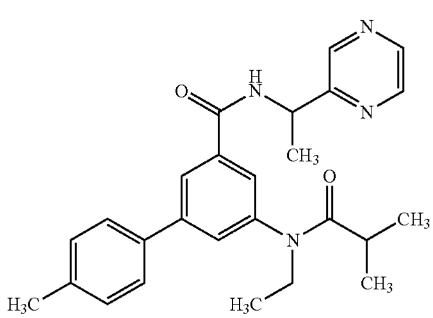 [SMILES: CCN(C(=O)C(C)C)c1cc(C(=O)NC(C)c2cnccn2)cc(-c2ccc(C)cc2)c1] | 5-(Ethyl-isobutyryl-amino)-4'-methyl-biphenyl-3-carboxylic acid (1-pyrazin-2-yl-ethyl)-amide | 8.11 |

TABLE 1-continued

| # | Structure | Name | P2X$_3$ |
|---|---|---|---|
| 39 | 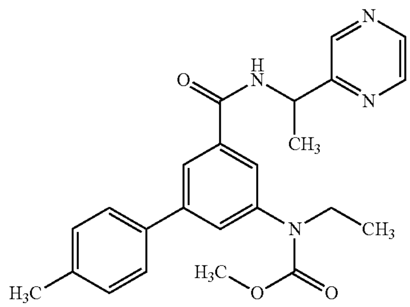 [SMILES: CCN(C(=O)OC)c1cc(C(=O)NC(C)c2cnccn2)cc(-c2ccc(C)cc2)c1] | Ethyl-[4'-methyl-5-(1-pyrazin-2-yl-ethylcarbamoyl)-biphenyl-3-yl]-carbamic acid methyl ester | 7.28 |
| 40 | 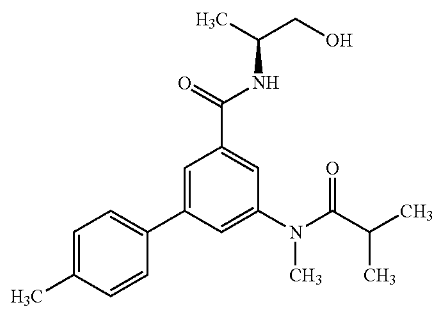 [SMILES: Cc1ccc(-c2cc(C(=O)N[C@@H](C)CO)cc(N(C)C(=O)C(C)C)c2)cc1] | 5-(Isobutyryl-methyl-amino)-4'-methyl-biphenyl-3-carboxylic acid ((S)-2-hydroxy-1-methyl-ethyl)-amide | 8.3 |
| 41 | 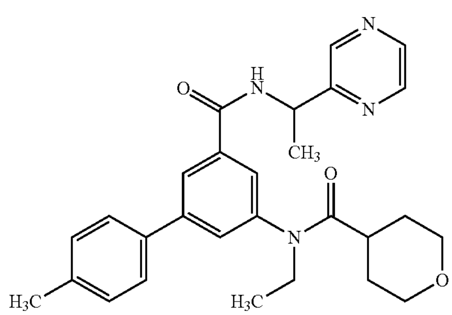 [SMILES: CCN(C(=O)C1CCOCC1)c1cc(C(=O)NC(C)c2cnccn2)cc(-c2ccc(C)cc2)c1] | Tetrahydro-pyran-4-carboxylic acid ethyl-[4'-methyl-5-(1-pyrazin-2-yl-ethylcarbamoyl)-biphenyl-3-yl]-amide | 6.86 |
| 42 | 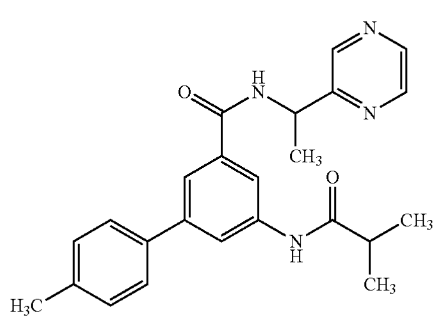 [SMILES: Cc1ccc(-c2cc(NC(=O)C(C)C)cc(C(=O)NC(C)c3cnccn3)c2)cc1] | 5-Isobutyrylamino-4'-methyl-biphenyl-3-carboxylic acid (1-pyrazin-2-yl-ethyl)-amide | 5.53 |
| 43 | 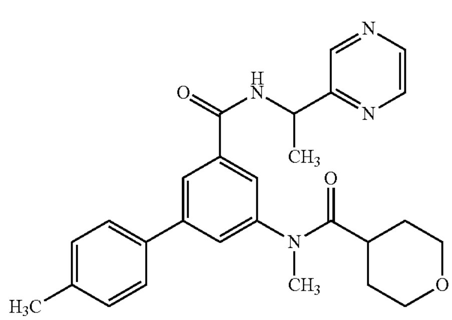 [SMILES: Cc1ccc(-c2cc(C(=O)NC(C)c3cnccn3)cc(N(C)C(=O)C3CCOCC3)c2)cc1] | Tetrahydro-pyran-4-carboxylic acid methyl-[4'-methyl-5-(1-pyrazin-2-yl-ethylcarbamoyl)-biphenyl-3-yl]-amide | 5.86 |

TABLE 1-continued

| # | Structure | Name | P2X$_3$ |
|---|---|---|---|
| 44 | 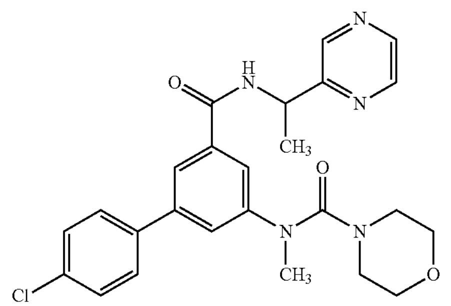 [SMILES: CC(NC(=O)c1cc(-c2ccc(Cl)cc2)cc(N(C)C(=O)N2CCOCC2)c1)c1cnccn1] | Morpholine-4-carboxylic acid [4'-chloro-5-(1-pyrazin-2-yl-ethylcarbamoyl)-biphenyl-3-yl]-methyl-amide | 5.17 |
| 45 | 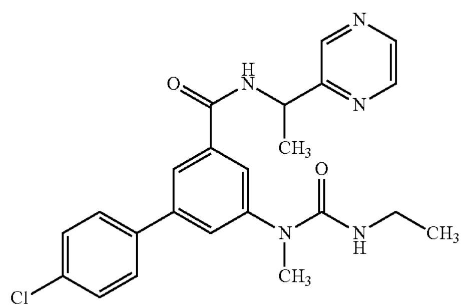 [SMILES: CCNC(=O)N(C)c1cc(C(=O)NC(C)c2cnccn2)cc(-c2ccc(Cl)cc2)c1] | 4'-Chloro-5-(3-ethyl-1-methyl-ureido)-biphenyl-3-carboxylic acid (1-pyrazin-2-yl-ethyl)-amide | 5.38 |
| 46 | 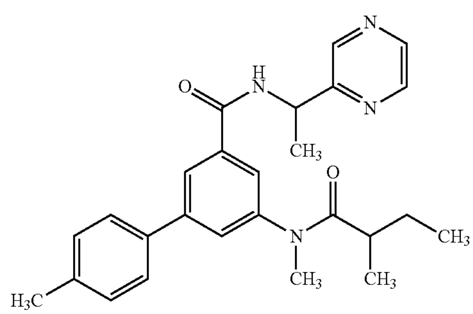 [SMILES: CCC(C)C(=O)N(C)c1cc(C(=O)NC(C)c2cnccn2)cc(-c2ccc(C)cc2)c1] | 4'-Methyl-5-[methyl-(2-methyl-butyryl)-amino]-biphenyl-3-carboxylic acid (1-pyrazin-2-yl-ethyl)-amide | 8.04 |
| 47 | 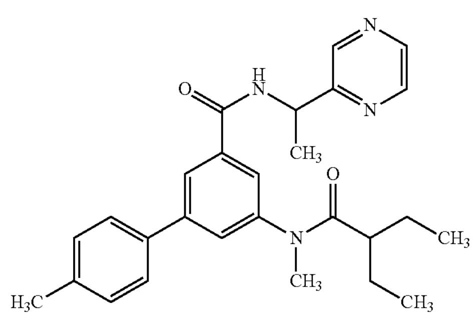 [SMILES: CCC(CC)C(=O)N(C)c1cc(C(=O)NC(C)c2cnccn2)cc(-c2ccc(C)cc2)c1] | 5-[(2-Ethyl-butyryl)-methyl-amino]-4'-methyl-biphenyl-3-carboxylic acid (1-pyrazin-2-yl-ethyl)-amide | 7.12 |
| 48 | 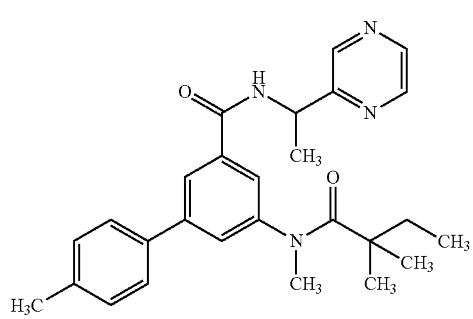 [SMILES: CCC(C)(C)C(=O)N(C)c1cc(C(=O)NC(C)c2cnccn2)cc(-c2ccc(C)cc2)c1] | 5-[(2,2-Dimethyl-butyryl)-methyl-amino]-4'-methyl-biphenyl-3-carboxylic acid (1-pyrazin-2-yl-ethyl)-amide | 7.55 |

TABLE 1-continued

| # | Structure | Name | P2X$_3$ |
|---|---|---|---|
| 49 | 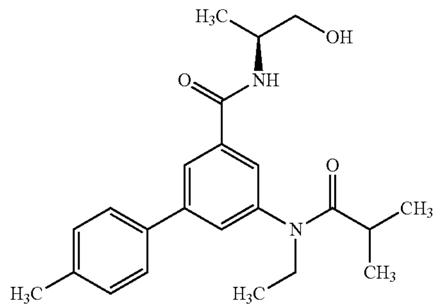 [SMILES: CCN(C(=O)C(C)C)c1cc(C(=O)N[C@@H](C)CO)cc(-c2ccc(C)cc2)c1] | 5-(Ethyl-isobutyryl-amino)-4'-methyl-biphenyl-3-carboxylic acid ((S)-2-hydroxy-1-methyl-ethyl)-amide | 8.38 |
| 50 | 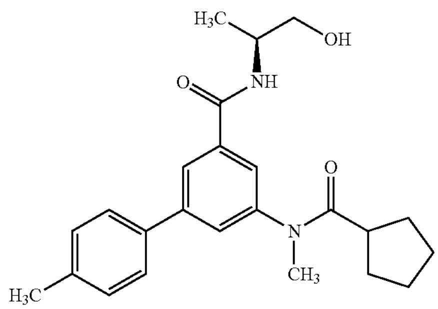 [SMILES: Cc1ccc(-c2cc(C(=O)N[C@@H](C)CO)cc(N(C)C(=O)C3CCCC3)c2)cc1] | 5-(Cyclopentanecarbonyl-methyl-amino)-4'-methyl-biphenyl-3-carboxylic acid ((S)-2-hydroxy-1-methyl-ethyl)-amide | 7.85 |
| 51 | 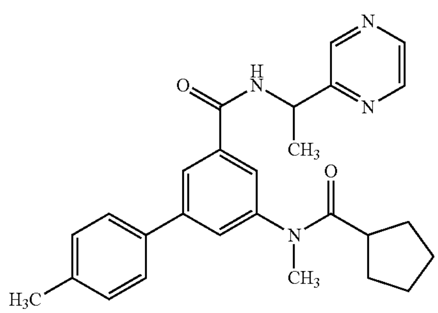 [SMILES: Cc1ccc(-c2cc(C(=O)NC(C)c3cnccn3)cc(N(C)C(=O)C3CCCC3)c2)cc1] | 5-(Cyclopentanecarbonyl-methyl-amino)-4'-methyl-biphenyl-3-carboxylic acid (1-pyrazin-2-yl-ethyl)-amide | 7.57 |
| 52 | 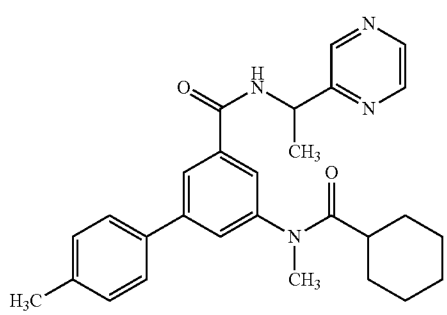 [SMILES: Cc1ccc(-c2cc(C(=O)NC(C)c3cnccn3)cc(N(C)C(=O)C3CCCCC3)c2)cc1] | 5-(Cyclohexanecarbonyl-methyl-amino)-4'-methyl-biphenyl-3-carboxylic acid (1-pyrazin-2-yl-ethyl)-amide | 5.9 |
| 53 | 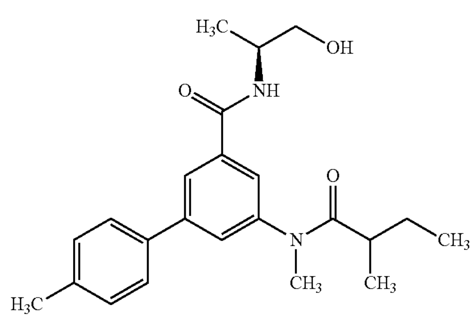 [SMILES: CCC(C)C(=O)N(C)c1cc(C(=O)N[C@@H](C)CO)cc(-c2ccc(C)cc2)c1] | 4'-Methyl-5-[methyl-(2-methyl-butyryl)-amino]-biphenyl-3-carboxylic acid ((S)-2-hydroxy-1-methyl-ethyl)-amide | 7.37 |

TABLE 1-continued

| # | Structure | Name | P2X$_3$ |
|---|---|---|---|
| 54 | 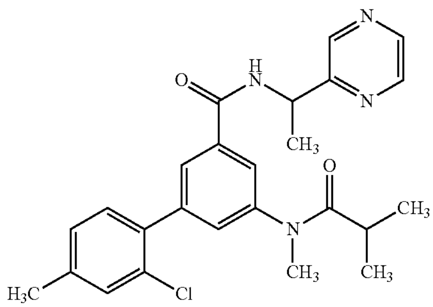 | 2'-Chloro-5-(isobutyryl-methyl-amino)-4'-methyl-biphenyl-3-carboxylic acid (1-pyrazin-2-yl-ethyl)-amide | 6.29 |
| 55 | 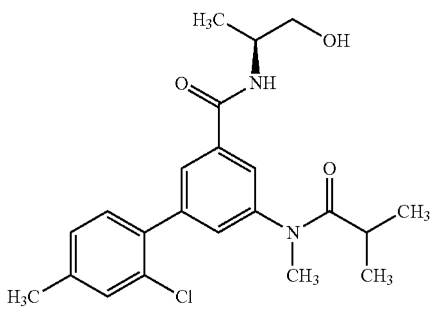 | 2'-Chloro-5-(isobutyryl-methyl-amino)-4'-methyl-biphenyl-3-carboxylic acid ((S)-2-hydroxy-1-methyl-ethyl)-amide | 5.53 |
| 56 | 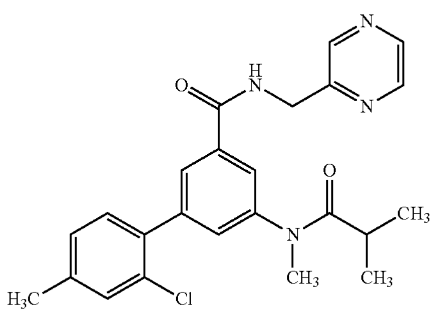 | 2'-Chloro-5-(isobutyryl-methyl-amino)-4'-methyl-biphenyl-3-carboxylic acid (pyrazin-2-ylmethyl)-amide | 5.6 |
| 57 | 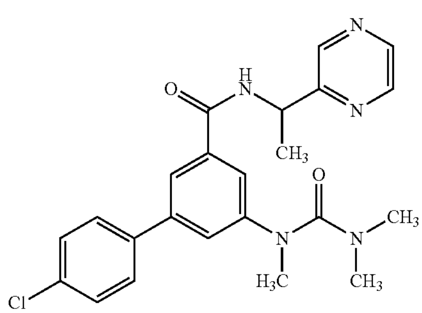 [SMILES: CC(NC(=O)c1cc(-c2ccc(Cl)cc2)cc(N(C)C(=O)N(C)C)c1)c1cnccn1] | 4'-Chloro-5-(trimethyl-ureido)-biphenyl-3-carboxylic acid (1-pyrazin-2-yl-ethyl)-amide | 6.26 |
| 58 | 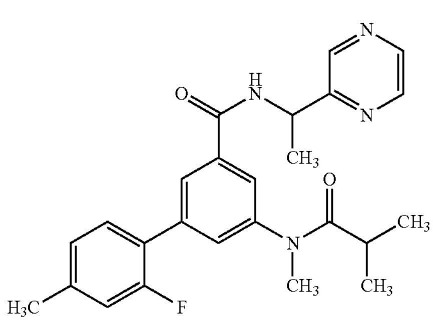 [SMILES: Cc1ccc(-c2cc(C(=O)NC(C)c3cnccn3)cc(N(C)C(=O)C(C)C)c2)c(F)c1] | 2'-Fluoro-5-(isobutyryl-methyl-amino)-4'-methyl-biphenyl-3-carboxylic acid (1-pyrazin-2-yl-ethyl)-amide | 8.25 |

TABLE 1-continued

| # | Structure | Name | P2X$_3$ |
|---|---|---|---|
| 59 | 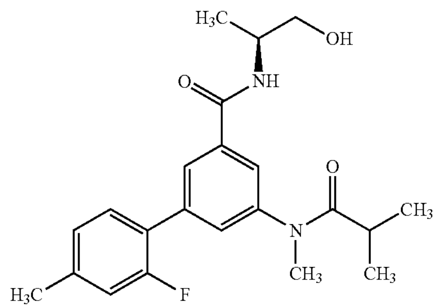 [SMILES: Cc1ccc(-c2cc(C(=O)N[C@@H](C)CO)cc(N(C)C(=O)C(C)C)c2)c(F)c1] | 2'-Fluoro-5-(isobutyryl-methyl-amino)-4'-methyl-biphenyl-3-carboxylic acid ((S)-2-hydroxy-1-methyl-ethyl)-amide | 8.16 |
| 60 | 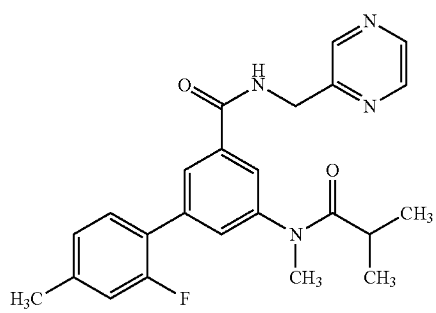 [SMILES: Cc1ccc(-c2cc(C(=O)NCc3cnccn3)cc(N(C)C(=O)C(C)C)c2)c(F)c1] | 2'-Fluoro-5-(isobutyryl-methyl-amino)-4'-methyl-biphenyl-3-carboxylic acid (pyrazin-2-ylmethyl)-amide | 7.8 |
| 61 | 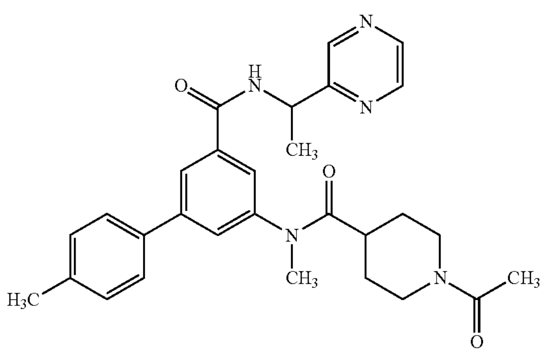 [SMILES: CC(=O)N1CCC(C(=O)N(C)c2cc(C(=O)NC(C)c3cnccn3)cc(-c3ccc(C)cc3)c2)CC1] | 1-Acetyl-piperidine-4-carboxylic acid methyl-[4'-methyl-5-(1-pyrazin-2-yl-ethylcarbamoyl)-biphenyl-3-yl]-amide | 5.7 |
| 62 | 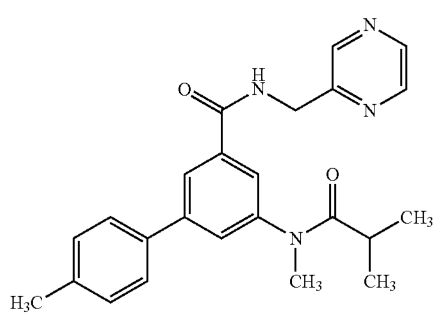 | 5-(Isobutyryl-methyl-amino)-4'-methyl-biphenyl-3-carboxylic acid (pyrazin-2-ylmethyl)-amide | 8.14 |
| 63 | 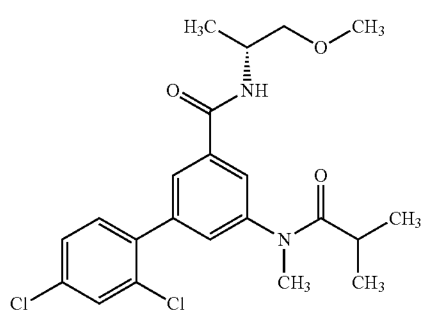 [SMILES: COC[C@@H](C)NC(=O)c1cc(-c2ccc(Cl)cc2Cl)cc(N(C)C(=O)C(C)C)c1] | 2',4'-Dichloro-5-(isobutyryl-methyl-amino)-biphenyl-3-carboxylic acid ((R)-2-methoxy-1-methyl-ethyl)-amide | 5.94 |

TABLE 1-continued

| # | Structure | Name | P2X$_3$ |
|---|---|---|---|
| 64 | 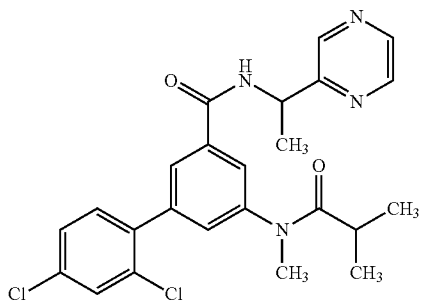 [SMILES: CC(C)C(=O)N(C)c1cc(C(=O)NC(C)c2cnccn2)cc(-c2ccc(Cl)cc2Cl)c1] | 2',4'-Dichloro-5-(isobutyryl-methyl-amino)-biphenyl-3-carboxylic acid (1-pyrazin-2-yl-ethyl)-amide | 7.5 |
| 65 | 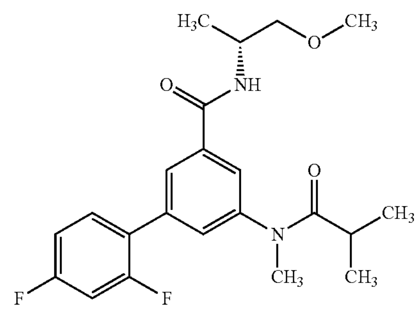 [SMILES: COC[C@@H](C)NC(=O)c1cc(-c2ccc(F)cc2F)cc(N(C)C(=O)C(C)C)c1] | 2',4'-Difluoro-5-(isobutyryl-methyl-amino)-biphenyl-3-carboxylic acid ((R)-2-methoxy-1-methyl-ethyl)-amide | 5.38 |
| 66 | 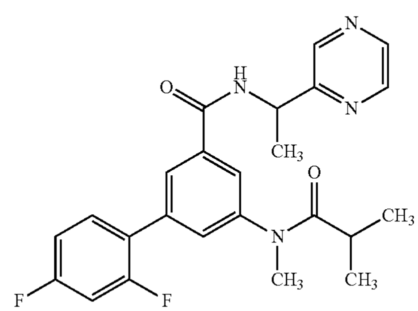 [SMILES: CC(C)C(=O)N(C)c1cc(C(=O)NC(C)c2cnccn2)cc(-c2ccc(F)cc2F)c1] | 2',4'-Difluoro-5-(isobutyryl-methyl-amino)-biphenyl-3-carboxylic acid (1-pyrazin-2-yl-ethyl)-amide | 6.63 |
| 67 | 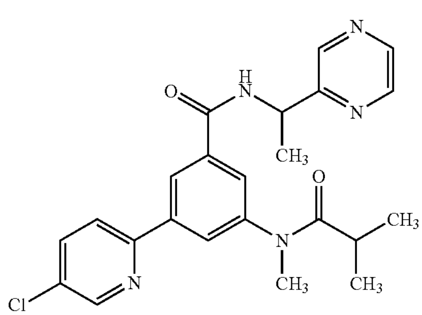 [SMILES: CC(C)C(=O)N(C)c1cc(C(=O)NC(C)c2cnccn2)cc(-c2ccc(Cl)cn2)c1] | 3-(5-Chloro-pyridin-2-yl)-5-(isobutyryl-methyl-amino)-N-(1-pyrazin-2-yl-ethyl)-benzamide | 7.75 |
| 68 | 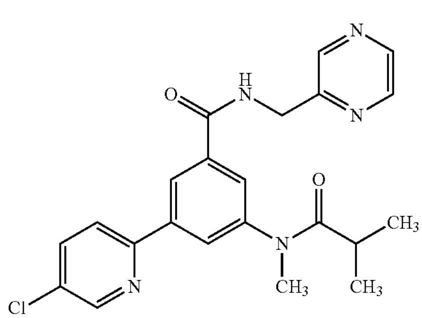 [SMILES: CC(C)C(=O)N(C)c1cc(C(=O)NCc2cnccn2)cc(-c2ccc(Cl)cn2)c1] | 3-(5-Chloro-pyridin-2-yl)-5-(isobutyryl-methyl-amino)-N-(5-methyl-pyrazin-2-ylmethyl)-benzamide | 7.93 |

TABLE 1-continued

| # | Structure | Name | P2X$_3$ |
|---|---|---|---|
| 69 | 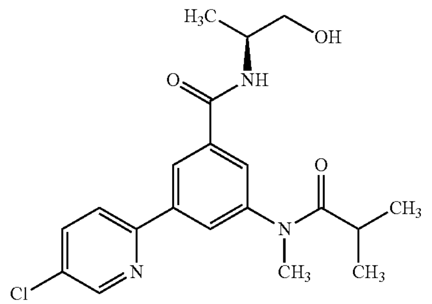 [SMILES: CC(C)C(=O)N(C)c1cc(C(=O)N[C@@H](C)CO)cc(-c2ccc(Cl)cn2)c1] | 3-(5-Chloro-pyridin-2-yl)-N-((S)-2-hydroxy-1-methyl-ethyl)-5-(isobutyryl-methyl-amino)-benzamide | 6.86 |
| 70 | 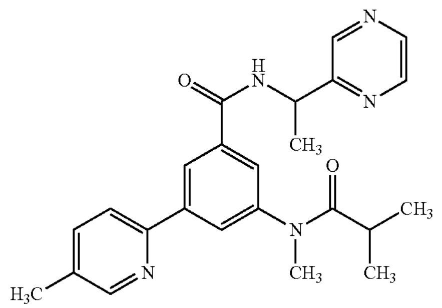 | 3-(Isobutyryl-methyl-amino)-5-(5-methyl-pyridin-2-yl)-N-(1-pyrazin-2-yl-ethyl)-benzamide | 8.11 |
| 71 | 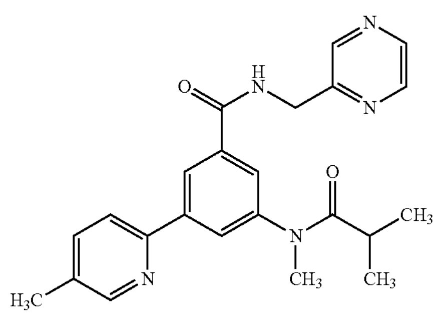 [SMILES: Cc1ccc(-c2cc(C(=O)NCc3cnccn3)cc(N(C)C(=O)C(C)C)c2)nc1] | 3-(Isobutyryl-methyl-amino)-N-(5-methyl-pyrazin-2-ylmethyl)-5-(5-methyl-pyridin-2-yl)-benzamide | 8.36 |
| 72 | 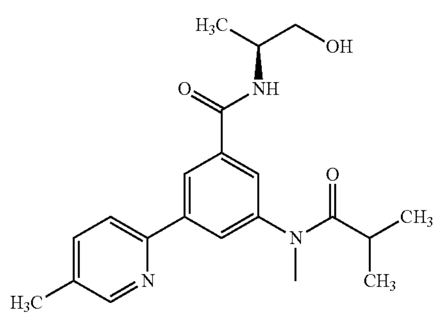 [SMILES: Cc1ccc(-c2cc(C(=O)N[C@@H](C)CO)cc(N(C)C(=O)C(C)C)c2)nc1] | N-((S)-2-Hydroxy-1-methyl-ethyl)-3-(isobutyryl-methyl-amino)-5-(5-methyl-pyridin-2-yl)-benzamide | 7.58 |
| 73 | 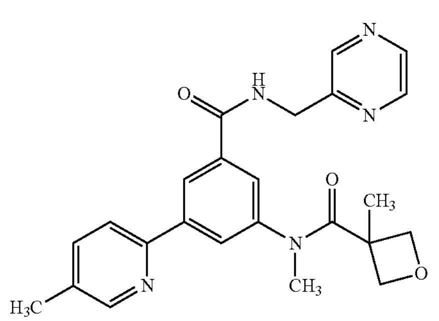 [SMILES: Cc1ccc(-c2cc(C(=O)NCc3cnccn3)cc(N(C)C(=O)C3(C)COC3)c2)nc1] | 3-Methyl-oxetane-3-carboxylic acid methyl-[3-[(5-methyl-pyrazin-2-ylmethyl)-carbamoyl]-5-(5-methyl-pyridin-2-yl)-phenyl]-amide | 7.09 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula I, wherein R is lower alkyl and X, $R^2$, $R^3$, $R^4$, $R^5$ and $R^{10}$ are as defined herein.

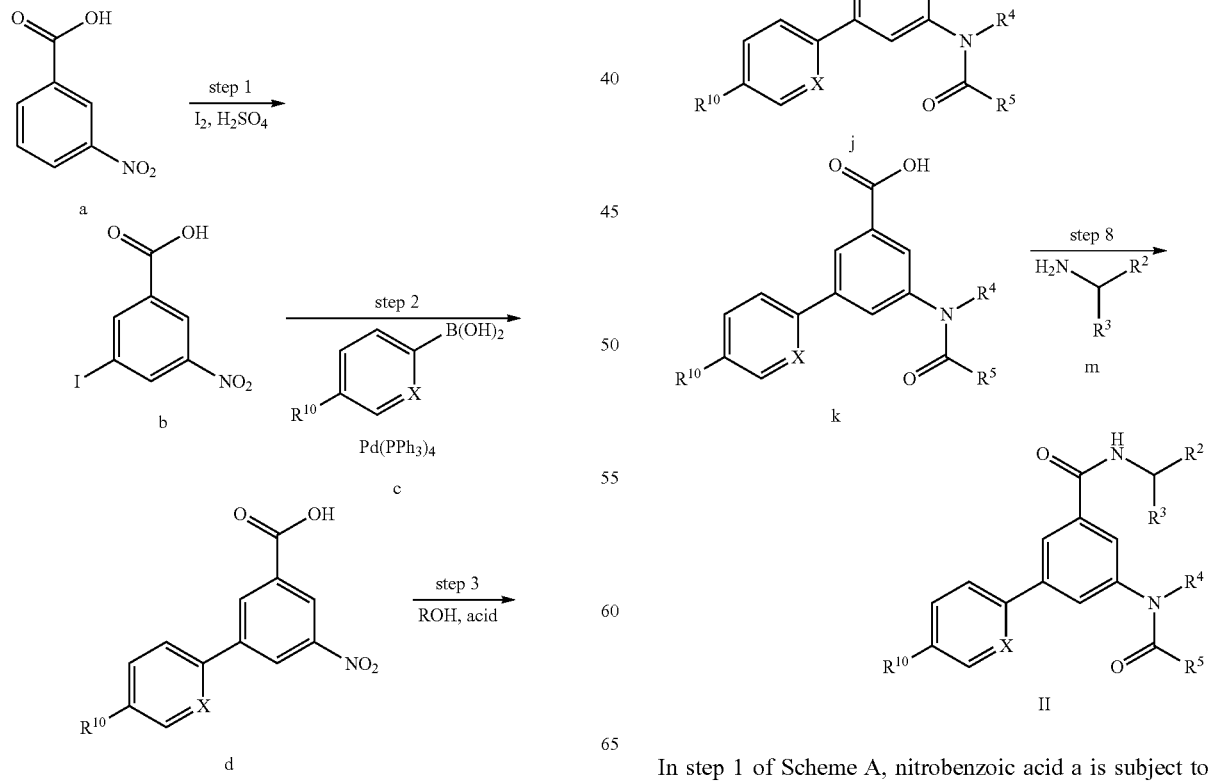

In step 1 of Scheme A, nitrobenzoic acid a is subject to iodination under sulfuric acid conditions to afford iodo-nitrobenzoic acid b. Benzoic acid compound b is reacted with arylboronic acid compound c in the presence of tetrakis-(triphenylphosphine)palladium catalyst to afford biphenyl acid compound d. The acid group of biphenyl acid d is protected by esterification in step 3 to form biphenyl acid methyl ester e. Biphenyl ester e is then subject to reduction to form biphenylamine f in step 4. An acylation takes place in step 5 wherein biphenylamine f is treated with acyl halide g to yield biphenyl amide compound h. In step 6 biphenyl amide h optionally undergoes an N-alkylation by reaction with alkyl halide i to give compound j. The ester group of compound j is hydrolized in step 7 to afford the corresponding acid compound k. In step 8 compound k undergoes an amide formation by reaction with amine m to afford compound II, which is a compound of formula I in accordance with the invention.

Many variations of Scheme A are possible and will suggest themselves to those skilled in the art. For example, in certain embodiments the boronic acid functionality of compound c may be interchanged with the halo functionality of compound b, as shown in Preparation 7 in the Examples below. In some embodiments step 6 may be omitted (to give compounds wherein $R^4$ is hydrogen). In other embodiments the alkylation of step 6 may be carried out prior to step 5. In still other embodiments an acid anhydride may be used in step 5 in place of acid halide g. Specific details for producing compounds of the invention are described in the Examples section below.

Utility

The compounds of the invention are usable for the treatment of a wide range of genitorurinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitits, pelvic pain syndrome, prostatodynia, cystitis, and idiophatic bladder hypersensitivity, and other symptoms related to overactive bladder.

The compounds of the invention are expected to find utility as analgesics in the treatment of diseases and conditions associated with pain from a wide variety of causes, including, but not limited to, inflammatory pain such as pain associated with arthritis (including rheumatoid arthritis and osteoarthritis), surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Further, compounds of the invention are useful for treating respiratory disorders, including chronic obstructive pulmonary disorder (COPD), asthma, bronchospasm, and the like.

Additionally, compounds of the invention are useful for treating gastrointestinal disorders, including Irritable Bowel Syndrome (IBS), Inflammatory Bowel Disease (IBD), biliary colic and other biliary disorders, renal colic, diarrhea-dominant IBS, pain associated with GI distension, and the like.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

ABBREVIATIONS

DBU 1,8-diazabicyclo[5.4.0]undec-7-ene
DCM dichloromethane/methylene chloride
DIPEA diisopropyl ethylamine
DME 1,2-dimethoxyethane (glyme)
DMF N,N-dimethylformamide
DMFDMA N,N-dimethylformamide dimethyl acetal
DMSO dimethyl sulfoxide
DMAP 4-dimethylaminopyridine
ECDI 1-ethyl-3-(3'-dimethylaminopropyl)carbodiimide
EtOAc ethyl acetate
EtOH ethanol
$Et_3N$ triethylamine
gc gas chromatography
HMPA hexamethylphosphoramide
HOBt N-Hydroxybenzotriazole
hplc high performance liquid chromatography
IPA isopropanol
mCPBA m-chloroperbenzoic acid
MeCN acetonitrile
NMM N-methyl morpholine
NMP N-methylpyrrolidinone
TEA triethylamine
THF tetrahydrofuran
LDA lithium diisopropylamine
TLC thin layer chromatography

Preparation 1

(S)-2-Methoxy-1-methyl-ethylamine

The synthetic procedure used in this preparation is outlined below in

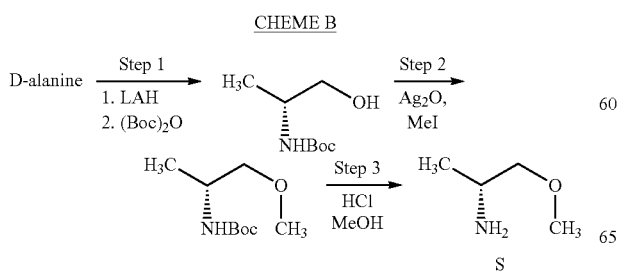

Step 1 (S)-Boc-2-amino-propanol

D-Alanine (3.5 g, 39.3 mmol) was added in small portions to a suspension of $LiAlH_4$ (2.89 g, 76.26 mmol) in refluxing THF. Refluxing continued for 12 hours, then the reaction mixture was cooled to 0° C., and excess reagent was quenched by careful addition of an aqueous 15% NaOH solution (3 ml) and water (9 ml). After stirring at room temperature for 10 minutes, a solution of $(Boc)_2O$ (8.31 g, 38.13 mmol) in $CH_2Cl_2$ (40 ml) was added. The reaction mixture was stirred at 60° C. for 6 hours, cooled to room temperature, filtered through a pad of anhydrous $Na_2SO_4$, and the filtrate concentrated under vacuum. Purification of the residue by silica-gel column chromatography afforded (S)-Boc-2-amino-propanol as a white solid, yield: 63%. MS (M+H)=176.

Step 2 (S)-Boc-2-methoxy-1-methyl-ethylamine

To a solution of (S)-Boc-2-amino-propanol (2.00 g, 11.4 mmol) was successively added $Ag_2O$ (5.89 g, 25.4 mmol) and Methyl iodide (16.00 g, 112.7 mmol) at room temperature. The reaction mixture was stirred at room temperature for 2 days. Solid was filtered off and the filtrate was concentrated under vacuum to afford (S)-Boc-2-methoxy-1-methyl-ethylamine as a colorless oil that was used without further purification.

Step 3 (S)-2-methoxy-1-methyl-ethylamine (S)-Boc-2-methoxy-1-methyl-ethylamine was dissolved in MeOH (40 mL) and 3 M HCl (10 mL) was added. The reaction mixture was stirred overnight at room temperature, then solvent was removed under reduced pressure and the residue was co-evaporated with additional EtOH (20 mL) to afford (S)-2-methoxy-1-methyl-ethylamine as light-brown oil in hydrochloride form (1.42 g, 100%). MS (M+H)=90.

Similarly prepared was (S)-2-ethoxy-1-methyl-ethylamine.

Similarly prepared from L-alanine were (R)-2-methoxy-1-methyl-ethylamine and (R)-2-ethoxy-1-methyl-ethylamine.

Preparation 2

(S)-1-Methyl-2-morpholin-4-yl-ethylamine

The synthetic procedure used in this preparation is outlined below in Scheme C.

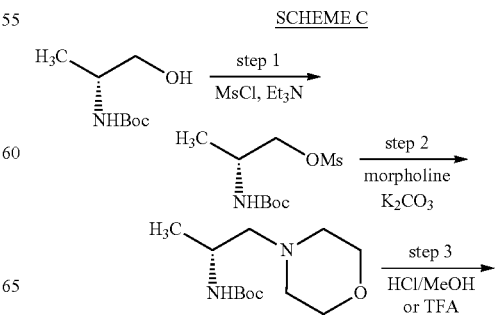

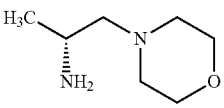

Step 1 Methanesulfonic acid 2-tert-butoxycarbonylamino-propyl ester

To a solution of (S)-Boc-2-amino-propanol (4.91 g, 0.028 mol), Et$_3$N (1.5 equiv.) in CH$_2$Cl$_2$ at 0° C. was added methanesulfonyl chloride (1.1-1.2 equiv). The reaction was stirred at 0° C. for 30 minutes. Water (5 ml) was added and the organic layer was separated, washed with saturated aqueous NaHCO$_3$, brine, and dried with MgSO$_4$. Solvent was removed under vacuum to afford methanesulfonic acid 2-tert-butoxycarbonylamino-propyl ester as a white solid, yield: 98%. MS (M+H)=254.

Step 2 (1-Methyl-2-morpholin-4-yl-ethyl)-carbamic acid tert-butyl ester

To a solution of methanesulfonic acid 2-tert-butoxycarbonylamino-propyl ester (23 mmol) in CH$_3$CN (20 mL) was added morpholine (28 mmol) and K$_2$CO$_3$ (23 mmol) at room temperature. The reaction mixture was brought to 50° C. and kept at the same temperature overnight. The reaction mixture was cooled and solvent was removed under reduced pressure, and the residue was treated with CH$_2$Cl$_2$ (50 mL) and H$_2$O (50 mL). The organic layer was separated and the aqueous layer was extracted with CH$_2$Cl$_2$. The combined organic layer was dried over Na$_2$SO$_4$. Solvent was removed under reduced pressure and the residue was purified by column chromatography (ethyl acetate) to afford (1-methyl-2-morpholin-4-yl-ethyl)-carbamic acid tert-butyl ester as viscous liquid, yield: 62%. MS (M+H)=245.

Step 3 (S)-1-Methyl-2-morpholin-4-yl-ethylamine

To a solution of (1-methyl-2-morpholin-4-yl-ethyl)-carbamic acid tert-butyl ester (0.30 g, 1.22 mmol) in methanol (10 mL) was added 2N HCl (5 mL) at 0° C. The reaction mixture was allowed to warm to room temperature and was stirred overnight. The solvent was removed under vacuum to give (S)-1-Methyl-2-morpholin-4-yl-ethylamine as a light yellow solid (250 mg, 96%). MS (M+H)=145.

Similarly prepared were (S)-1-Methyl-2-thiomorpholin-4-yl-ethylamine, (S)-1-[4-(2-Amino-propyl)-piperazin-1-yl]-ethanone, (S)-1-(2-Amino-propyl)-piperidin-4-ol, (S)-1-(2-Amino-propyl)-piperidin-3-ol, (S)-1-Methyl-2-(4-methyl-piperazin-1-yl)-ethylamine, (S)-1-Methyl-2-(4-methanesulfonyl-piperazin-1-yl)-ethylamine, (S)-4-(2-Amino-propyl)-piperazin-2-one, 1-Methyl-2-piperidin-1-yl-ethylamine, 1-(2-Amino-propyl)-pyrrolidin-3-ol, (S)-2-(4-Methoxy-piperidin-1-yl)-1-methyl-ethylamine, (S)-2-(3-Methoxy-piperidin-1-yl)-1-methyl-ethylamine, (S)-2-(4-Methanesulfonyl-piperidin-1-yl)-1-methyl-ethylamine, and other 2-amino-1-heterocyclyl propanes.

Preparation 3

1-Pyrazin-2-yl-ethylamine

The synthetic procedure used in this preparation is outlined below in Scheme D.

SCHEME D

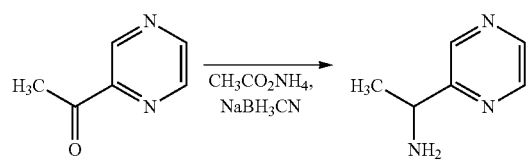

To a solution of 1-pyrazin-2-yl-ethanone (2.0 g, 15.85 mmol) and ammonium acetate (19.337 g, 158.5 mmol) in methanol (50 mL) was added sodium cyanoborohydride (0.7 g, 11.1 mmol) in one portion. The reaction mixture was stirred overnight at room temperature. After removal of methanol, water (20 mL) was added to the residue and the resulting solution was basified by addition of sodium hydroxide to pH=13. The aqueous solution was extracted with dicholromethane and the combined organic phase was dried over sodium sulfate. Removal of the solvent under reduced pressure afforded 14.62 g of 1-pyrazin-2-yl-ethylamine, yield: 75%. MS (M+H)=124.

Similarly prepared from the appropriate heteroaryl methyl ketones or phenyl methyl ketones were: 1-pyridin-2-yl-ethylamine, 1-pyridin-3-yl-ethylamine, 1-pyridin-4-yl-ethylamine, 1-(2-fluoro-phenyl)-ethylamine, 1-(3-Fluoro-phenyl)-ethylamine, 1-(4-methanesulfonyl-phenyl)-ethylamine, 1-thien-3-yl-ethylamine, 1-furan-2-yl-ethylamine, 1-(5-methyl-furan)-2-yl-ethylamine, 1-thiazol-2-yl-ethylamine, 1-thien-2-yl-ethylamine, 1-pyrimidin-2-yl-ethylamine, C-(6-methyl-pyridazin-3-yl)-methylamine, C-(5-methyl-pyrazin-2-yl)-methylamine, and 1-pyridazin-4-yl-ethylamine.

Preparation 4

5-Amino-4'-methyl-biphenyl-3-carboxylic acid (2-methoxy-1-methyl-ethyl)-amide The synthetic procedure used in this preparation is outlined below in Scheme E.

SCHEME E

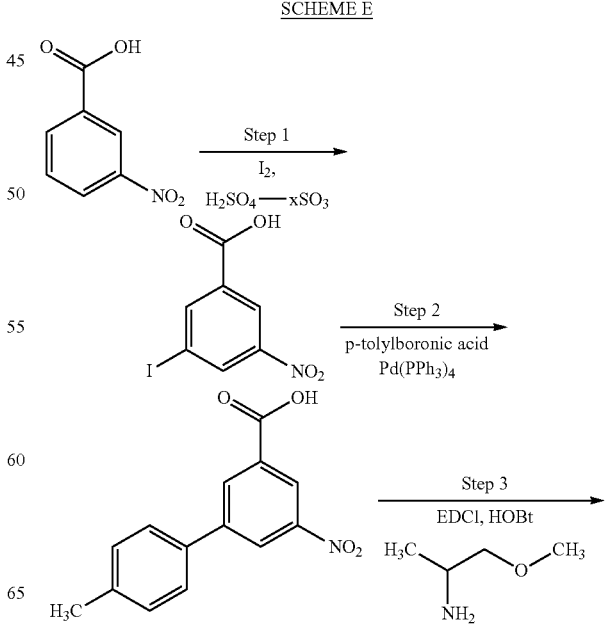

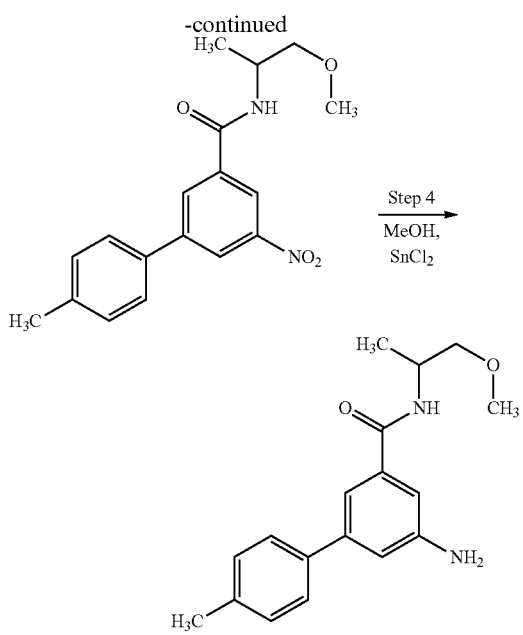

Step 1 3-Iodo-5-nitro-benzoic acid

To a stirred solution of iodine (137.95 g, 0.5436 mmol) in fuming sulfuric acid (250 ml) was added m-nitrobenzoic acid (64.6 g, 0.3866 mmol) at room temperature. The reaction mixture was slowly heated to 85° C. overs 2 hours and stirred at the same temperature for another 12 hours. The reaction mixture was cooled to room temperature and poured into ice, and the aqueous solution was extracted with dichloromethane. The organic phase was separated and washed with water, 2.0 M solution of $Na_2S_2O_3$ and brine, and then dried over $Na_2SO_4$. Solvent was removed under reduced pressure to yield 3-iodo-5-nitrobenzoic acid as slight yellow solid 111 g, yield 98%. MS (M+H)=294.

Step 2 4'-Methyl-5-nitro-biphenyl-3-carboxylic acid

To a stirred solution of 3-iodo-5-nitrobenzoic acid (15.48 g, 52.83 mmol) and $Pd(Ph_3P)_4$ (1.84 g, 1.69 mmol) in 300 ml of toluene and 50 ml of ethanol was added p-tolylboronic acid (7.87 g, 58.11 mmol) and a solution of $Cs_2CO_3$ (18.89 g, 58.11 mmol) in 20 ml water at room temperature. The reaction was brought to reflux for 18 hours and then cooled to room temperature. To the solution was added 2N NaOH, and the reaction mixture was stirred for 30 minutes. The organic phase was separated, and the aqueous phase was adjusted to PH<4 using 12N HCl. The resulting solid preciptate was filtered and washed with toluene to afford 13.2 g of 4'-methyl-5-nitro-biphenyl-3-carboxylic acid as light yellow solid (97.2%). MS (M+H)=258.

Step 3 4'-Methyl-5-nitro-biphenyl-3-carboxylic acid (2-methoxy-1-methyl-ethyl)-amide EDCI (16.17 g, 84.38 mmol) was added portion wise to a stirred solution of 4'-methyl-5-nitro-biphenyl-3-carboxylic acid (15.49 g, 60.27 mmol), HOBt (11.44 g, 84.38 mmol) and 2-amino-1-methoxy-1-propane (7 ml, 66.31 mmol) in NMP (9.29 ml, 84.38 mmol), $CH_2Cl_2$ (180 ml) and DMF (20 ml) at 0° C. The mixture was allowed to warm to room temperature and was stirred at the same temperature for 14 hours. The reaction mixture was washed with 2N HCl, 2N NaOH, saturated aqueous $NaHCO_3$, brine, dried over anhydrous $Na_2SO_4$, filtered, and concentrated under vacuum to give 4'-methyl-5-nitro-biphenyl-3-carboxylic acid (2-methoxy-1-methyl-ethyl)-amide as a yellow oil (16.5 g, 83.5%). MS (M+H)=329.

Step 4 5-Amino-4'-methyl-biphenyl-3-carboxylic acid (2-methoxy-1-methyl-ethyl)-amide To a stirred solution of 4'-methyl-5-nitro-biphenyl-3-carboxylic acid (2-methoxy-1-methyl-ethyl)-amide (39 mmol) in 250 ml methanol was added $SnCl_2$ (117 mmol) in one portion at room temperature. The reaction mixture was heated to reflux for 3 hours. Solvent was removed under reduced pressure and the residue was diluted with ethyl acetate and treated with saturated $NaHCO_3$ solution. Solids were filtered off and the filtrate was washed with saturated aqueous $NaHCO_3$, brine, dried over anhydrous $Na_2SO_4$, filtered and concentrated in vaccuo to give 5-amino-4'-methyl-biphenyl-3-carboxylic acid (2-methoxy-1-methyl-ethyl)-amide as a yellow oil (10.5 g, 90.3%). MS (M+H)=299.

Preparation 5

5-Amino-4'-methyl-biphenyl-3-carboxylic acid methyl ester

The synthetic procedure used in this preparation is outlined below in

SCHEME F

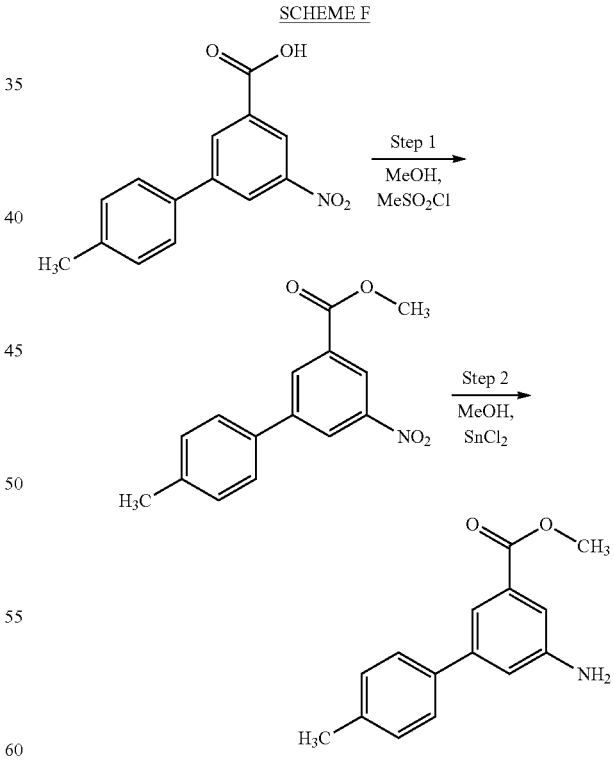

Step 1, 4'-Methyl-5-nitro-biphenyl-3-carboxylic acid methyl ester

To a solution of 4'-methyl-5-nitro-biphenyl-3-carboxylic acid (10.00 g, 0.039 mol) in methanol was added $SOCl_2$ (5.09 g, 0.043 mol) at 0° C. The reaction mixture was allowed to warm to room temperature and was then heated to reflux for 2 hours. The solvent was removed in vacuo to afford 4'-Methyl-5-nitro-biphenyl-3-carboxylic acid methyl ester (9.72 g, 92%) as light yellow solid. MS (M+H)=273.

Step 2 5-Amino-4'-methyl-biphenyl-3-carboxylic acid methyl ester

4'-Methyl-5-nitro-biphenyl-3-carboxylic acid methyl ester was reduced using SnCl₂ using the procedure of step 4 of preparation 4 to afford 5-amino-4'-methyl-biphenyl-3-carboxylic acid methyl ester, MS (M+H)=242.

Preparation 7

3-Amino-5-(5-methyl-pyridin-2-yl)-benzoic acid methyl ester

The synthetic procedure used in this preparation is outlined below in Scheme G.

SCHEME G

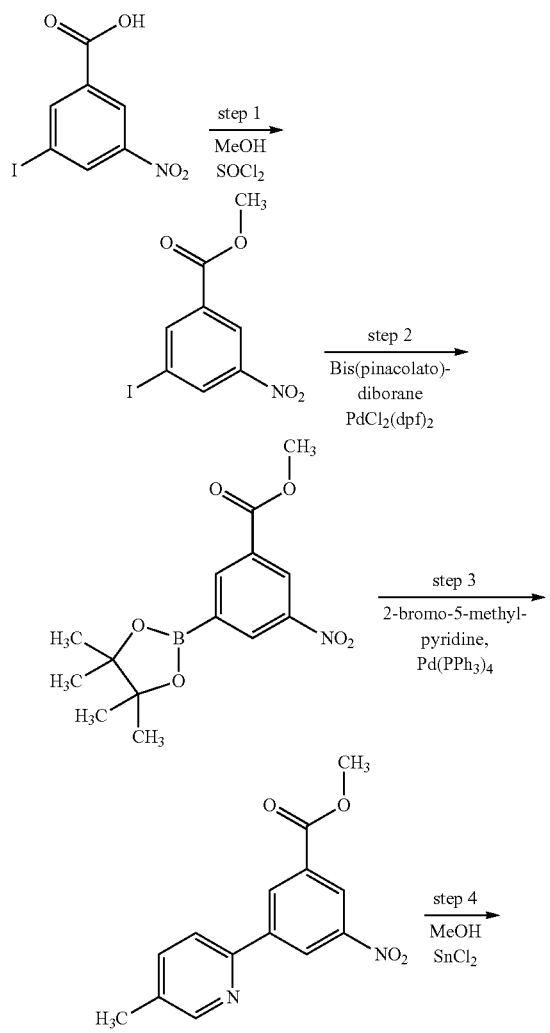

-continued

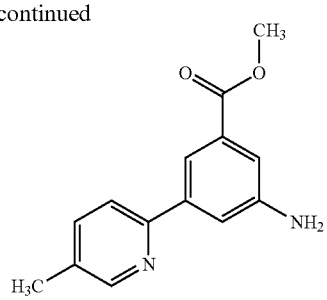

Step 1 3-Iodo-5-nitro-benzoic acid methyl ester

To a solution of 3-iodo-5-nitrobenzoic acid (20.00 g, 0.068 mol) in methanol (50 mL) was added SOCl₂ (5.45 mL, 0.075 mol) at 0° C. The reaction mixture was allowed to warm to room temperature and was then heated to breflux for 2 hours. The reaction was cooled and solvent was removed in vacuo to afford 3-Iodo-5-nitro-benzoic acid methyl ester as light yellow solid (20.67 g, 99%). MS (M+H)=309.

Step 2 3-Nitro-5-(4,4,5,5-tetramethyl-[1,3,2]dioxaborolan-2-yl)-benzoic acid methyl ester A solution of 3-iodo-5-nitro-benzoic acid methyl ester (10 g, 0.0326 mol), bis(pinacolato)diboron (9.1 g, 0.0358 mol), KOAc (9.5 9 g, 0.098 mol) and PdCl₂(dppf) (798 mg, 0.98 mmol) in DMSO (40 ml) was heated to 80° C. for 4 hours under N₂ atmosphere. The mixture was cooled to room temperature and extracted with Et₂O. The combined organic phases were washed with brine and dried over Na₂SO₄. The solvent was evaporated under reduced pressure and the resulting crude 3-nitro-5-(4,4,5,5-tetramethyl-[1,3,2]dioxaborolan-2-yl)-benzoic acid methyl ester was used without purification in the next step.

Step 3 3-(5-Methyl-pyridin-2-yl)-5-nitro-benzoic acid methyl ester

To a solution of 2-bromo-5-methylpyridine (1.24 g, 7 mmol), Pd(PPh₃)₄ (226 mg, 0.2 mmol) and K₃PO₄ (2.76 g, 13 mmol) in DME/H₂O (5 ml/1 ml) was added 3-nitro-5-(4,4,5,5-tetramethyl-[1,3,2]dioxaborolan-2-yl)-benzoic acid methyl ester (2.00 g, 6.5 mmol) under N₂ atmosphere. The mixture was subjected to microwave radiation at 130° C. for 0.5 hours. The reaction mixture was cooled and solvent was evaporated under reduced pressure. The residue was purified by flash-chromatography (CH₂Cl₂/MeOH) to give 3-(5-methyl-pyridin-2-yl)-5-nitro-benzoic acid methyl ester as a white solid (700 mg, 40%).

Step 4 3-Amino-5-(5-methyl-pyridin-2-yl)-benzoic acid methyl ester

To a solution of 3-(5-methyl-pyridin-2-yl)-5-nitro-benzoic acid methyl ester (4 g, 14.7 mmol) in methanol/ethyl acetate was added SnCl₂ (11.15 g, 58.8 mmol) at room temperature. The reaction mixture was refluxed for 3 hours and then cooled. Solvent was removed under reduced pressure and the residue was dissolved in H₂O and basified by addition of Na₂CO₃ to pH=9. The mixture was extracted with CH₂Cl₂, and the organic phase was washed with water, brine, and dried over Na₂SO₄. The solvent was removed under reduced pressure to give 3-amino-5-(5-methyl-pyridin-2-yl)-benzoic acid methyl ester (3.2 g, 90%) as white solid.

Similarly prepared was 3-amino-5-(5-chloro-pyridin-2-yl)-benzoic acid methyl ester.

Example 1

5-(Isobutyryl-methyl-amino)-4'-methyl-biphenyl-3-carboxylic acid (1-pyrazin-2-yl-ethyl)-amide The synthetic procedure used in this preparation is outlined below in Scheme H.

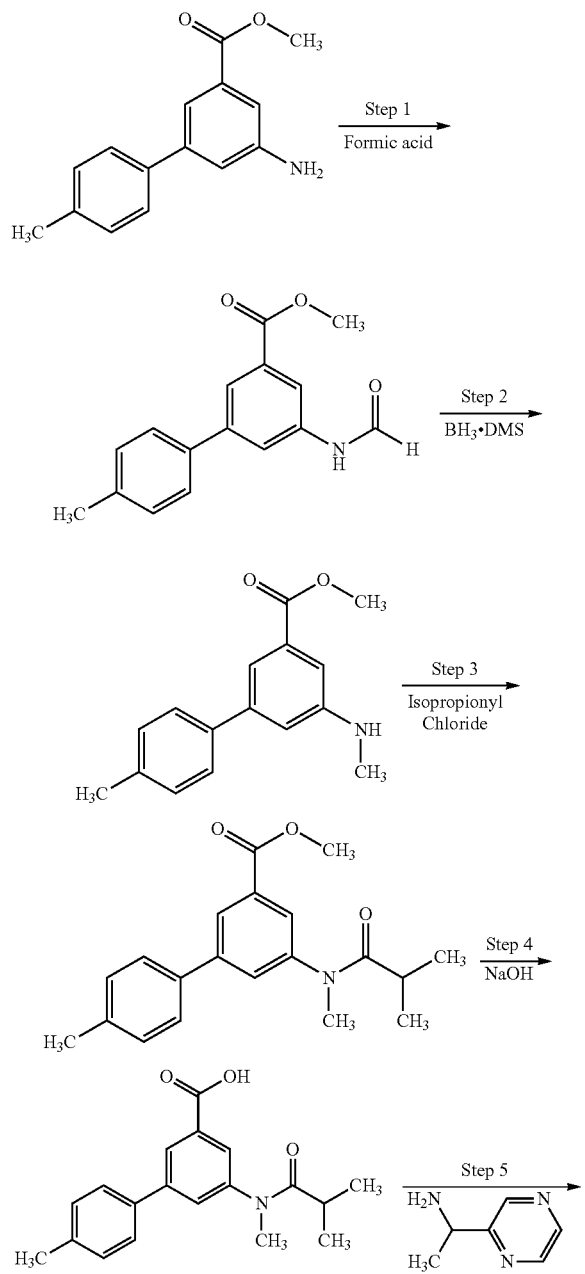

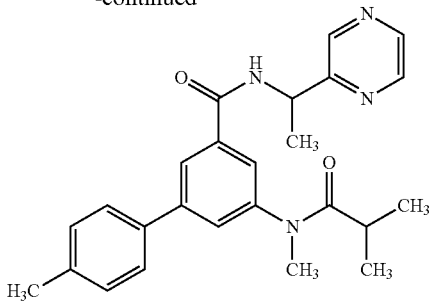

Step 1 5-Formylamino-4'-methyl-biphenyl-3-carboxylic acid methyl ester

Acetic anhydride (11.0 g, 108 mmol) was added to THF (15 mL) followed by addition of formic acid (5.09 g, 133 mmol). The mixture was heated to 65° C. for 2.5 hours, then cooled to room temperature. 5-Amino-4'-methyl-biphenyl-3-carboxylic acid methyl ester (5.0 g, 21 mmol) was added, and the reaction mixture was stirred for three hours at 70° C., then cooled to room temperature. The reaction mixture was diluted with water and extracted with ethyl acetate. The combined organic extracts were washed with brine, dried over MgSO$_4$, filtered and concentrated under reduced pressure to give 5-formylamino-4'-methyl-biphenyl-3-carboxylic acid methyl ester, which was used directly in the next step without further purification.

Step 2 4'-Methyl-5-methylamino-biphenyl-3-carboxylic acid methyl ester

4'-Methyl-5-methylamino-biphenyl-3-carboxylic acid methyl ester (5.3 g, mmol) in THF (50 mL) was heated to 60° C. BH$_3$-dimethyl sulfide (2.95 mL of 10M solution in THF, 30 mmol) was added sloly via syringe. The reaction mixture was heated to 75° C. for 90 minutes with stirring. The reaction mixture was cooled, diluted with CH$_3$OH (50 mL), and stirred for 30 minutes. The mixture was then diluted with water, and extracted with ethyl acetate. The combined organic extracts were washed with saturated aqueous sodium bicarbonate and brine, dried over MgSO$_4$, filtered and concentrated under reduced pressure to give 4.9 g of 4'-methyl-5-methylamino-biphenyl-3-carboxylic acid methyl ester as a white solid.

Step 3 5-(Isobutyryl-methyl-amino)-4'-methyl-biphenyl-3-carboxylic acid methyl ester 4'-Methyl-5-methylamino-biphenyl-3-carboxylic acid methyl ester (1.0 g, 4 mmol) and triethylamine (0.79 g, 8 mmol) were added to methylene chloride (15.0 mL) and stirred. Isopbutyryl chloride (0.459 g, 4 mmol) was added, together with DMAP (0.1 g). The reaction mixture was stirred overnight at room temperature, then diluted with methylene chloride and washed with 1N aqueous HCl and brine, dried over MgSO$_4$, filtered and concentrated under reduced pressure to give 1.1 g of 5-(sobutyryl-methyl-amino)-4'-methyl-biphenyl-3-carboxylic acid methyl ester as a white foam.

Step 4 5-(Isobutyryl-methyl-amino)-4'-methyl-biphenyl-3-carboxylic acid 5-(Isobutyryl-methyl-amino)-4'-methyl-biphenyl-3-carboxylic acid methyl ester (85 mg, 0.26 mmol)) was added to a mixture of methanol (2 mL) and 1N aqueous NaOH (2 mL) and the mixture was stirred for one hour. HCl (1N aqueous solution) was added dropwise to the stirring solution until a precipitate formed. An additional 0.5 1M of 1N HCl was added, and the mixture was extracted with ethyl acetate. The combined organic extracts were washed with brine, dried over MgSO$_4$, filtered and concentrated under reduced pressure to give 67 mg of 5-(isobutyryl-methyl-amino)-4'-methyl-biphenyl-3-carboxylic acid.

Step 5 5-(Isobutyryl-methyl-amino)-4'-methyl-biphenyl-3-carboxylic acid (1-pyrazin-2-yl-ethyl)-amide 5-(Isobutyryl-methyl-amino)-4'-methyl-biphenyl-3-carboxylic acid methyl ester (67 mg, 0.22 mmol) was added to methylene chloride (3 mL) and stirred at room temperature. TEA (0.87 g), 1-pyrazin-2-yl-ethylamine (32 mg, 0.25 mmol), HOBt (29 mg) and ECDI (54 mg) were added, and the reaction mixture was stirred overnight at room temperature. The reaction mixture was placed directly onto a silica column and eluted with 50% ethyl acetate/hexanes to give 32 mg of 5-(isobutyryl-methyl-amino)-4'-methyl-biphenyl-3-carboxylic acid (1-pyrazin-2-yl-ethyl)-amide as a white solid, MS (M+H)=417.

Similarly prepared, using 3-amino-5-(5-methyl-pyridin-2-yl)-benzoic acid methyl ester in place of 5-amino-4'-methyl-biphenyl-3-carboxylic acid methyl ester, was 3-(isobutyryl-methyl-amino)-5-(5-methyl-pyridin-2-yl)-N-(1-pyrazin-2-yl-ethyl)-benzamide, MS (M+H)=418.

Similarly prepared, using acetyl chloride in place of isobutyryl chloride, was 5-(acetyl-methyl-amino)-4'-methyl-biphenyl-3-carboxylic acid (1-pyrazin-2-yl-ethyl)-amide, MS (M+H)=389.

Similarly prepared, using 2,2-dimethyl-propionyl chloride in place of isobutyryl chloride, was 5-[(2,2-dimethyl-propionyl)-methyl-amino]-4'-methyl-biphenyl-3-carboxylic acid (1-pyrazin-2-yl-ethyl)-amide, MS (M+H)=431.

Similarly prepared, using C-pyrazin-2-yl-methylamine in place of 1-pyrazin-2-yl-ethylamine, was 5-(Isobutyryl-methyl-amino)-4'-methyl-biphenyl-3-carboxylic acid (pyrazin-2-ylmethyl)-amide, MS (M+H)=403.

Additional compounds prepared using the above procedure are shown in Table 1.

Example 2

5-(Ethyl-isobutyryl-amino)-4'-methyl-biphenyl-3-carboxylic acid (1-pyrazin-2-yl-ethyl)-amide The synthetic procedure used in this preparation is outlined below in Scheme I.

SCHEME I

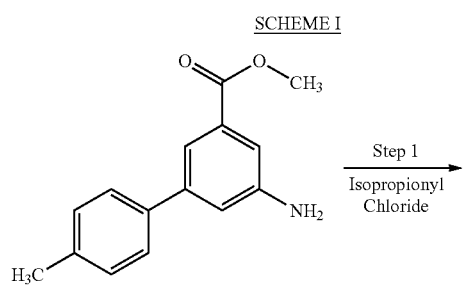

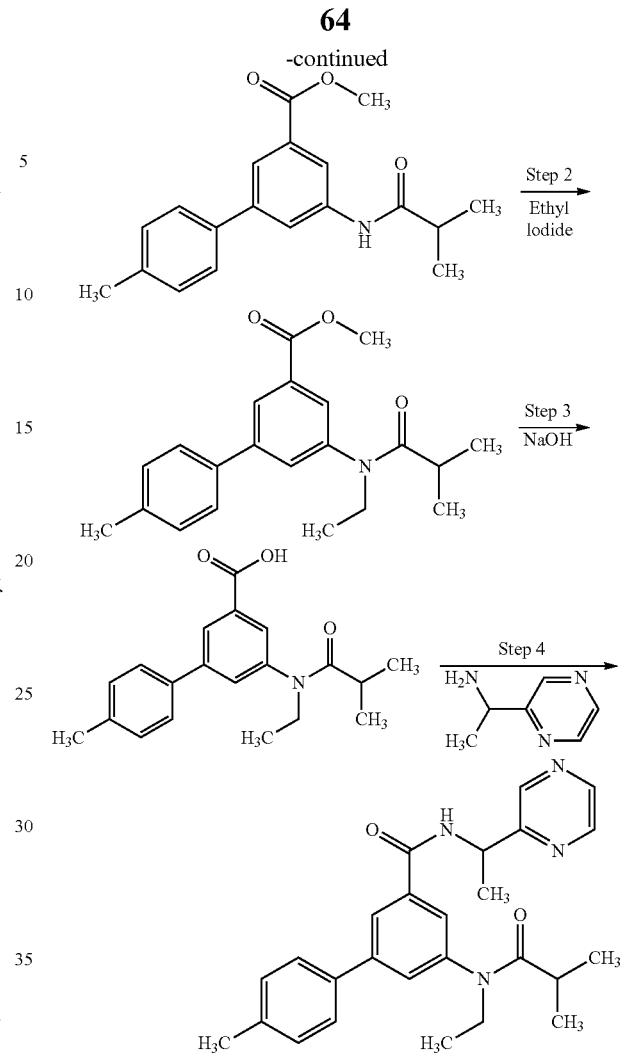

Step 1 5-Isobutyrylamino-4'-methyl-biphenyl-3-carboxylic acid methyl ester

5-Amino-4'-methyl-biphenyl-3-carboxylic acid methyl ester (0.10 g, 2.49 mmol) and triethylamine (6.75 g, 7.47 mmol) were added to dichloromethane (40 mL) and stirred under nitrogen atmosphere. Isobutyryl chloride (0.318 g, 2.98 mmol) was added slowly, and the reaction mixture was stirred for 2.5 hours at room temperature. The mixture was diluted with water and 1N aqueous HCl, and the organic layer was separated, washed with water and brine, dried over MgSO$_4$, filtered and concentrated under reduced pressure to give 0.786 g of 5-isobutyrylamino-4'-methyl-biphenyl-3-carboxylic acid methyl ester.

Step 2 5-(Ethyl-isobutyryl-amino)-4'-methyl-biphenyl-3-carboxylic acid methyl ester 5-Isobutyrylamino-4'-methyl-biphenyl-3-carboxylic acid methyl ester (0.786 g, 2.32 mmol) and NaH (6.2 g, 2.55 mmol) were added to DMF (20 mL), and the mixture was stirred for 30 minutes at room temperature, then cooled to 0° C. Ethyl iodide (1.181 g, 11.6 mmol) was added, and the reaction mixture was stirred for five days at room temperature. The reaction was quenched by addition of saturated aqueous NH$_4$Cl and water, and the mixture was extracted with diethyl ether. The combined organic layers were separated, washed with water and brine, dried over MgSO$_4$, filtered and concentrated under reduced pressure. The residue was purified by flash chromatography (30% ethyl acetate in hexanes) to give 0.461 g of 5-(ethyl-isobutyryl-amino)-4'-methyl-biphenyl-3-carboxylic acid methyl ester.

Step 3 5-(Ethyl-isobutyryl-amino)-4'-methyl-biphenyl-3-carboxylic acid 5-(Ethyl-isobutyryl-amino)-4'-methyl-biphenyl-3-carboxylic acid methyl ester (0.461 g, 1.36 mmol) was dissolved in THF (10 mL). To this THF solution was added a solution of LiOH (0.342 g) in water (8 mL). The mixture was stirred at 50° C. for three hours, then cooled to room temperature. The mixture was acidified by addition of 1N aqueous HCl and extracted with ethyl acetate. The combined organic extracts were washed with brine, dried over MgSO$_4$, filtered and concentrated under reduced pressure to give 0.46 g of 5-(ethyl-isobutyryl-amino)-4'-methyl-biphenyl-3-carboxylic acid as a clear foam.

Step 4 5-(Ethyl-isobutyryl-amino)-4'-methyl-biphenyl-3-carboxylic acid (1-pyrazin-2-yl-ethyl)-amide 5-(Ethyl-isobutyryl-amino)-4'-methyl-biphenyl-3-carboxylic acid was reacted with 1-pyrazin-2-yl-ethylamine following the procedure of step 5 of Example 1 to give 5-(ethyl-isobutyryl-amino)-4'-methyl-biphenyl-3-carboxylic acid (1-pyrazin-2-yl-ethyl)-amide, MS (M+H)=431.

Similarly prepared, replacing isobutyryl chloride with 3-methyl-butyryl chloride, was 5-[ethyl-(3-methyl-butyryl)-amino]-4'-methyl-biphenyl-3-carboxylic acid (1-pyrazin-2-yl-ethyl)-amide, MS (M+H)=445.

Additional compounds prepared using the above procedure are shown in Table 1.

Example 3

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 4

P2X$_3$/P2X$_{2/3}$ FLIPR (Fluorometric Imaging Plate Reader) Assay

CHO-K1 cells were transfected with cloned rat P2X$_3$ or human P2X$_{2/3}$ receptor subunits and passaged in flasks. 18-24 hours before the FLIPR experiment, cells were released from their flasks, centrifuged, and resuspended in nutrient medium at $2.5 \times 10^5$ cells/ml. The cells were aliquoted into black-walled 96-well plates at a density of 50,000 cells/well and incubated overnight in 5% $CO_2$ at 37° C. On the day of the experiment, cells were washed in FLIPR buffer (calcium- and magnesium-free Hank's balanced salt solution, 10 mM HEPES, 2 mM $CaCl_2$, 2.5 mM probenecid; FB). Each well received 100 l FB and 100 l of the fluorescent dye Fluo-3 AM [2 M final conc.]. After a 1 hour dye loading incubation at 37° C., the cells were washed 4 times with FB, and a final 75 μl/well FB was left in each well.

Test compounds (dissolved in DMSO at 10 mM and serially diluted with FB) or vehicle were added to each well (25 μl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 μl/well agonist or vehicle addition. The agonist was a 2× solution of α,β-meATP producing a final concentration of 1 μM (P2X$_3$) or 5 μM (P2X$_{2/3}$). Fluorescence was measured for an additional 2 minutes at 1 second intervals after agonist addition. A final addition of ionomycin (5 μM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above procedure, compounds of the invention exhibited activity for the P2X$_3$ and P2X$_{2/3}$ receptors as shown in Table 1.

Example 5

In vivo Assay for Asthma and Lung Function

BALb/cJ mice are immunized with a standard immunization protocol. Briefly, mice (N=8/group) are immunized i.p. with ovalbumin (OVA; 10 μg) in alum on days 0 and 14. Mice are then challenged with aerosolized OVA (5%) on day 21 and 22. Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

Example 6

Volume Induced Bladder Contraction Assay

Female Sprague-Dawley rats (200-300 g) were anesthetized with urethane (1.5 g/kg, sc). The animals were tracheotomized, and a carotid artery and femoral vein were cannulated for blood pressure measurement and drug administration, respectively. A laparotomy was performed and the ureters were ligated and transected proximal to the ligation. The external urethral meatus was ligated with silk suture and the urinary bladder was cannulated via the dome for saline infusion and bladder pressure measurement.

Following a 15-30 minute stabilization period the bladder was infused with room temperature saline at 100 μl/min until continuous volume-induced bladder contractions (VIBCs) were observed. The infusion rate was then lowered to 3-5 μl/min for 30 minutes before the bladder was drained and allowed to rest for 30 minutes. All subsequent infusions were performed as indicated except the lower infusion rate was maintained for only 15 minutes instead of 30 minutes. Bladder filling and draining cycles were repeated until the threshold volumes (TV; the volume needed to trigger the first micturition bladder contraction) varied by less than 10% for two consecutive baselines and contraction frequency was within 2 contractions for a 10 minute period following the slower infusion rate. Once reproducible TVs and VIBCs were established the bladder was drained and the animal was dosed with drug or vehicle (0.5 ml/kg, i.v.) 3 minutes prior to the start of the next scheduled infusion.

Example 7

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 μl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 min bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 8

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

Example 9

Cold Allodynia in Rats with a Chronic Constriction Injury of the Sciatic Nerve

The effects of compounds of this invention on cold allodynia are determined using the chronic constriction injury (CCI) model of neuropathic pain in rats, where cold allodynia is measured in a cold-water bath with a metal-plate floor and water at a depth of 1.5-2.0 cm and a temperature of 3-4° C. (Gogas, K. R. et al., Analgesia, 1997, 3, 1-8).

Specifically, CCI, rats are anesthetized; the trifurcation of the sciatic nerve is located and 4 ligatures (4-0, or 5-0 chromic gut) are placed circumferentially around the sciatic nerve proximal to the trifurcation. The rats are then allowed to recover from the surgery. On days 4-7 after surgery, the rats are initially assessed for cold-induced allodynia by individually placing the animals in the cold-water bath and recording the total lifts of the injured paw during a 1-min period of time: The injured paw is lifted out of the water. Paw lifts associated with locomotion or body repositioning are not recorded. Rats that displayed 5 lifts per min or more on day 4-7 following surgery are considered to exhibit cold allodynia and are used in subsequent studies. In the acute studies, vehicle, reference compound or compounds of this invention are administered subcutaneously (s.c.) 30 min before testing. The effects of repeated administration of the compounds of this invention on cold allodynia are determined 14, 20 or 38 h following the last oral dose of the following regimen: oral (p.o.) administration of vehicle, reference or a compound of this invention at −12 h intervals (BID) for 7 days.

Example 10

Cancer Bone Pain in C3H/HeJ Mice

The effects of compounds of this invention on bone pain are determined between Day 7 to Day 18 following intramedullary injection of 2472 sarcoma cells into the distal femur of C3H/HeJ mice.

Specifically, NCTC 2472 tumor cells (American Type Culture Collection, ATCC), previously shown to form lytic lesions in bone after intramedullary injection, are grown and maintained according to ATCC recommendations. Approximately $10^5$ cells are injected directly into the medullary cavity of the distal femur in anesthetized C3H/HeJ mice. Beginning on about Day 7, the mice are assessed for spontaneous nocifensive behaviors (flinching & guarding), palpation-evoked nocifensive behaviors (flinching & guarding), forced ambulatory guarding and limb use. The effects of compounds of this invention are determined following a single acute (s.c.) administration on Day 7-Day 15. In addition, the effects of repeated (BID) administration of compounds of this invention from Day 7-Day 15 are determined within 1 hour of the first dose on Days 7, 9, 11, 13 and 15.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present inven-

What is claimed is:
1. A compound of formula I

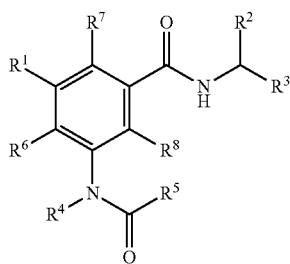

wherein:
$R^1$ is:
  pyridinyl substituted with methyl or halo at the 5-position;
$R^2$ is:
  hydrogen; or
  $C_{1-6}$alkyl;
$R^3$ is:
  $C_{1-6}$alkyl;
  hydroxy-$C_{1-6}$alkyl;
  $C_{1-6}$alkoxy-$C_{1-6}$alkyl;
  halo-$C_{1-6}$alkyl;
  $C_{3-7}$cycloalkyl;
  heteroaryl which may be substituted once or twice with methyl;
  heterocyclyl;
  heterocyclyl-$C_{1-6}$alkyl; or
  $C_{3-7}$cycloalkyl-$C_{1-6}$alkyl;
or $R^2$ and $R^3$ together form a $C_{3-7}$cycloalkyl;
$R^4$ is:
  hydrogen;
  $C_{1-6}$alkyl;
  $C_{3-7}$cycloalkyl;
  $C_{3-7}$cycloalkyl-$C_{1-6}$alkyl; or
  pyrimidinyl;
$R^5$ is:
  $C_{1-6}$alkyl;
  $C_{1-6}$alkoxy;
  $C_{3-7}$cycloalkyl;
  $C_{1-6}$alkoxy-$C_{1-6}$alkyl;
  amino-$C_{1-6}$alkyl;
  oxetanyl which may be substituted once or twice with $C_{1-6}$alkyl;
  phenyl which may be substituted once or twice with a group or groups independently selected from $C_{1-6}$alkyl, halo, halo-$C_{1-6}$alkyl and $C_{1-6}$alkoxy;
  thienyl which may be substituted once or twice with a group or groups independently selected from $C_{1-6}$alkyl and $C_{1-6}$alkoxy;
  furanyl which may be substituted once or twice with $C_{1-6}$alkyl;
  thiazolyl which may be substituted once or twice with $C_{1-6}$alkyl;
  oxazolyl which may be substituted once or twice with $C_{1-6}$alkyl;
  isoxazolyl which may be substituted once or twice with a group or groups independently selected from $C_{1-6}$alkyl and phenyl;
  pyrazolyl which may be substituted once or twice with $C_{1-6}$alkyl;
  thiadiazolyl which may be substituted once with $C_{1-6}$alkyl;
  tetrahydropyranyl;
  morpholinyl;
  piperidinyl which may be substituted with $C_{1-6}$alkyl or acetyl;
  pyrimidinyl; or
  pyridinyl which may be substituted once or twice with $C_{1-6}$alkyl; and
$R^6$, $R^7$ and $R^8$ each independently is:
  hydrogen; or
  halo.

2. The compound of claim 1, wherein said compound is of formula II:

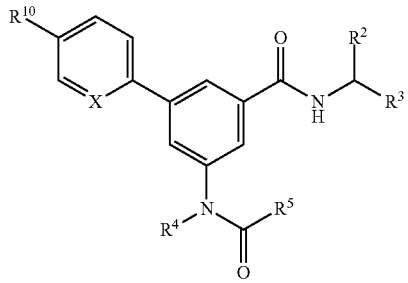

wherein:
  X is —N—; and
  $R^{10}$ is methyl or halo.

3. The compound of claim 2, wherein $R^2$ is hydrogen.
4. The compound of claim 2, wherein $R^2$ is methyl.
5. The compound of claim 2, wherein $R^3$ is: $C_{1-6}$alkyl; $C_{1-6}$alkoxy-$C_{1-6}$alkyl; hydroxy-$C_{1-6}$alkyl; heteroaryl; or heterocyclyl-$C_{1-6}$alkyl.
6. The compound of claim 2, wherein $R^3$ is: $C_{1-6}$alkoxy-$C_{1-6}$alkyl; hydroxy-$C_{1-6}$alkyl; heteroaryl, or heterocyclyl-$C_{1-6}$alkyl.
7. The compound of claim 2, wherein $R^3$ is methoxymethyl.
8. The compound of claim 2, wherein $R^3$ is hydroxymethyl.
9. The compound of claim 2, wherein $R^3$ is heteroaryl selected from pyridinyl, pyrimidinyl, or pyrazinyl, each of which may be substituted once or twice with methyl.
10. The compound of claim 2, wherein $R^3$ is hydroxymethyl, methoxymethyl, pyrazin-2-yl or 5-methyl-pyrazin-2-yl.
11. The compound of claim 2, wherein $R^5$ is $C_{1-6}$alkyl, or $C_{3-7}$cycloalkyl.
12. The compound of claim 2, wherein $R^5$ is isopropyl, isobutyl or tert-butyl.
13. The compound of claim 1, wherein $R^6$, $R^7$ and $R^8$ are hydrogen.
14. The compound of claim 1, wherein $R^1$ is 5-methyl-pyridin-2-yl.
15. The compound of claim 1, wherein said compound is selected from:
  3-(5-Chloro-pyridin-2-yl)-5-(isobutyryl-methyl-amino)-N-(1-pyrazin-2-yl-ethyl)-benzamide;
  3-(5-Chloro-pyridin-2-yl)-5-(isobutyryl-methyl-amino)-N-(5-methyl-pyrazin-2-ylmethyl)-benzamide;
  3-(5-Chloro-pyridin-2-yl)-N-((S)-2-hydroxy-1-methyl-ethyl)-5-(isobutyryl-methyl-amino)-benzamide;

3-(Isobutyryl-methyl-amino)-5-(5-methyl-pyridin-2-yl)-N-(1-pyrazin-2-yl-ethyl)-benzamide 3-(Isobutyryl-methyl-amino)-N-(5-methyl-pyrazin-2-ylmethyl)-5-(5-methyl-pyridin-2-yl)-benzamide;

N-((S)-2-Hydroxy-1-methyl-ethyl)-3-(isobutyryl-methyl-amino)-5-(5-methyl-pyridin-2-yl)-benzamide; and 3-Methyl-oxetane-3-carboxylic acid methyl-[3-[(5-methyl-pyrazin-2-ylmethyl)-carbamoyl]-5-(5-methyl-pyridin-2-yl)-phenyl]-amide.

16. A pharmaceutical composition comprising:

(a) a pharmaceutically acceptable carrier; and (b) a compound of claim 1.

* * * * *